United States Patent [19]
Keevert, Jr. et al.

[11] Patent Number: 5,580,712
[45] Date of Patent: Dec. 3, 1996

[54] SILVER HALIDE EMULSIONS, ELEMENTS AND METHODS OF MAKING SAME USING SYNTHETIC BIOPOLYMER PEPTIZERS

[75] Inventors: John E. Keevert, Jr., Rochester, N.Y.; Shane C. Weber, Woodbridge, Conn.; Ramesh Jagannathan, Rochester, N.Y.; Gerald W. Klein, Issaquah, Wash.

[73] Assignee: Eastman Kodak Company, Rochester, N.Y.

[21] Appl. No.: 383,348

[22] Filed: Feb. 3, 1995

[51] Int. Cl.$^6$ .......................... G03C 1/015; G03C 1/047; C12P 21/00
[52] U.S. Cl. .......................... 430/569; 430/567; 430/642; 435/69.1
[58] Field of Search .................................. 430/567, 569, 430/642; 435/69.1

[56] References Cited

U.S. PATENT DOCUMENTS

| | | | |
|---|---|---|---|
| 2,710,805 | 6/1955 | Wood | 430/642 |
| 4,315,072 | 2/1982 | Fox et al. | 430/640 |
| 4,713,320 | 12/1987 | Maskasky | 430/567 |
| 4,746,594 | 5/1988 | Kasama et al. | 430/642 |
| 4,898,810 | 2/1990 | Eggert et al. | 430/642 |
| 5,284,744 | 2/1994 | Maskasky | 430/569 |
| 5,380,642 | 1/1995 | Roberts et al. | 430/642 |
| 5,385,819 | 1/1995 | Bowman et al. | 430/642 |
| 5,439,791 | 8/1995 | Kok et al. | 430/642 |
| 5,496,712 | 3/1996 | Cappello et al. | 435/69.1 |

FOREIGN PATENT DOCUMENTS 2685347  6/1993  France.

OTHER PUBLICATIONS

Futuretech® Briefing No. 78, Mar. 27, 1989.
Mann, *Nature*, vol. 332, pp. 119–124, 1988.
Heuer et al, *Science*, vol. 255, pp. 1098–1105.
Addadi et al, *Angew. Chem. Int. Ed. Engl.*, vol. 31, pp. 153–169, 1992.
Mann et al, *Science*, vol. 261, pp. 1286–1292, 1993.

*Primary Examiner*—Mark F. Huff
*Attorney, Agent, or Firm*—J. Lanny Tucker

[57] ABSTRACT

Certain synthetically prepared biopolymers are useful as peptizers in the preparation of photographic silver halide emulsions and elements. Such materials can be used as either nucleation or growth peptizers in place of common peptizing colloids, such as gelatins. The biopolymers can be prepared using recombinant or chemical synthetic methods and designed to have a particular affinity (either high or low) for silver ions. Thus, they can be used to control silver halide grain morphology in the emulsions.

28 Claims, 5 Drawing Sheets

SEQUENCE LISTING ( 1 ) GENERAL INFORMATION:

( i i i ) NUMBER OF SEQUENCES: 20

( 2 ) INFORMATION FOR SEQ ID NO:1:

( i ) SEQUENCE CHARACTERISTICS:
       ( A ) LENGTH: 93
       ( B ) TYPE: Amino acid
       ( D ) TOPOLOGY: Linear ( i i ) MOLECULE TYPE: Polypeptide ( i i i ) HYPOTHETICAL: No ( i v ) ANTI-SENSE: No ( v ) FRAGMENT TYPE: C-terminal ( v i ) ORIGINAL SOURCE: Saccharomyces
                            cerevisiae ( v i i ) IMMEDIATE SOURCE: Saccharomyces
                               cerevisiae ( x ) PUBLICATION INFORMATION: None ( x i ) SEQUENCE DESCRIPTION: SEQ ID NO:1:

```
Gly Pro Glu Gly Pro Gln Gly Pro Glu Gly Pro Glu
                  5                    10
Gly Pro Glu Gly Pro Glu Gly Pro Gln Gly Pro Glu
            15                 20
Gly Pro Glu Gly Pro Glu Gly Pro Glu Gly Pro Gln
 25                30                    35
Gly Pro Glu Gly Pro Glu Gly Pro Glu Gly Pro Glu
            40                    45
Gly Pro Gln Gly Pro Glu Gly Pro Glu Gly Pro Glu
      50                 55                    60
Gly Pro Glu Gly Pro Gln Gly Pro Glu Gly Pro Glu
                  65                   70
Gly Pro Glu Gly Pro Glu Gly Pro Gln Gly Pro Glu
            75                 80
Gly Pro Glu Gly Pro Glu Gly Pro Glu
 85                      90
```

( 2 ) INFORMATION FOR SEQ ID NO:2:

( i ) SEQUENCE CHARACTERISTICS:
       ( A ) LENGTH: 123
       ( B ) TYPE: Amino acid
       ( D ) TOPOLOGY: Linear ( i i ) MOLECULE TYPE: Polypeptide ( i i i ) HYPOTHETICAL: No ( i v ) ANTI-SENSE: No ( v ) FRAGMENT TYPE: C-terminal ( v i ) ORIGINAL SOURCE: Saccharomyces
                            cerevisiae ( v i i ) IMMEDIATE SOURCE: Saccharomyces
cerevisiae ( x ) PUBLICATION INFORMATION: None ( x i ) SEQUENCE DESCRIPTION: SEQ ID NO:2:

| Gly | Pro | Glu | Gly | Pro | Gln | Gly | Pro | Glu | Gly | Pro | Glu |
|-----|-----|-----|-----|-----|-----|-----|-----|-----|-----|-----|-----|
|     |     |     |     | 5   |     |     |     | 10  |     |     |     |
| Gly | Pro | Glu | Gly | Pro | Glu | Gly | Pro | Gln | Gly | Pro | Glu |
|     |     |     | 15  |     |     |     |     | 20  |     |     |     |
| Gly | Pro | Glu | Gly | Pro | Glu | Gly | Pro | Glu | Gly | Pro | Gln |
| 25  |     |     |     |     | 30  |     |     |     |     |     | 35  |
| Gly | Pro | Glu | Gly | Pro | Glu | Gly | Pro | Glu | Gly | Pro | Glu |
|     |     |     |     | 40  |     |     |     | 45  |     |     |     |
| Gly | Pro | Gln | Gly | Pro | Glu | Gly | Pro | Glu | Gly | Pro | Glu |
|     |     | 50  |     |     |     |     | 55  |     |     |     | 60  |
| Gly | Pro | Glu | Gly | Pro | Gln | Gly | Pro | Glu | Gly | Pro | Glu |
|     |     |     |     | 65  |     |     |     |     | 70  |     |     |
| Gly | Pro | Glu | Gly | Pro | Glu | Gly | Pro | Gln | Gly | Pro | Glu |
|     |     |     | 75  |     |     |     |     | 80  |     |     |     |
| Gly | Pro | Glu | Gly | Pro | Glu | Gly | Pro | Glu | Gly | Pro | Gln |
| 85  |     |     |     |     |     |     | 90  |     |     |     | 95  |
| Gly | Pro | Glu | Gly | Pro | Glu | Gly | Pro | Glu | Gly | Pro | Glu |
|     |     |     |     | 100 |     |     |     |     | 105 |     |     |
| Gly | Pro | Gln | Gly | Pro | Glu | Gly | Pro | Glu | Gly | Pro | Glu |
|     |     | 110 |     |     |     |     | 115 |     |     |     | 120 |
| Gly | Pro | Glu |     |     |     |     |     |     |     |     |     |

( 2 ) INFORMATION FOR SEQ ID NO:3:

( i ) SEQUENCE CHARACTERISTICS:
( A ) LENGTH: 273
( B ) TYPE: Amino acid
( D ) TOPOLOGY: Linear ( i i ) MOLECULE TYPE: Polypeptide ( i i i ) HYPOTHETICAL: No ( i v ) ANTI-SENSE: No ( v ) FRAGMENT TYPE: C-terminal ( v i ) ORIGINAL SOURCE: Saccharomyces
cerevissiae ( v i i ) IMMEDIATE SOURCE: Saccharomyces
cerevissiae ( x ) PUBLICATION INFORMATION: None ( x i ) SEQUENCE DESCRIPTION: SEQ ID NO:3:

| Gly | Pro | Glu | Gly | Pro | Gln | Gly | Pro | Glu | Gly | Pro | Glu |
|-----|-----|-----|-----|-----|-----|-----|-----|-----|-----|-----|-----|
|     |     |     |     | 5   |     |     |     | 10  |     |     |     |
| Gly | Pro | Glu | Gly | Pro | Glu | Gly | Pro | Gln | Gly | Pro | Glu |
|     |     |     | 15  |     |     |     |     | 20  |     |     |     |
| Gly | Pro | Glu | Gly | Pro | Glu | Gly | Pro | Glu | Gly | Pro | Gln |
| 25  |     |     |     |     | 30  |     |     |     |     |     | 35  |
| Gly | Pro | Glu | Gly | Pro | Glu | Gly | Pro | Glu | Gly | Pro | Glu |
|     |     |     |     | 40  |     |     |     | 45  |     |     |     |
| Gly | Pro | Gln | Gly | Pro | Glu | Gly | Pro | Glu | Gly | Pro | Glu |
|     |     | 50  |     |     |     |     | 55  |     |     |     | 60  |

Gly Pro Glu Gly Pro Gln Gly Pro Glu Gly Pro Glu
              65                    70

Gly Pro Glu Gly Pro Glu Gly Pro Gln Gly Pro Glu
            75                80

Gly Pro Glu Gly Pro Glu Gly Pro Glu Gly Pro Gln
85                      90                      95

Gly Pro Glu Gly Pro Glu Gly Pro Glu Gly Pro Glu
            100                   105

Gly Pro Gln Gly Pro Glu Gly Pro Glu Gly Pro Glu
            110             115                 120

Gly Pro Glu Gly Pro Gln Gly Pro Glu Gly Pro Glu
                125                 130

Gly Pro Glu Gly Pro Glu Gly Pro Gln Gly Pro Glu
            135                 140

Gly Pro Glu Gly Pro Glu Gly Pro Glu Gly Pro Gln
145                 150                     155

Gly Pro Glu Gly Pro Glu Gly Pro Glu Gly Pro Glu
                160                 165

Gly Pro Gln Gly Pro Glu Gly Pro Glu Gly Pro Glu
            170             175                 180

Gly Pro Glu Gly Pro Gln Gly Pro Glu Gly Pro Glu
                185                     190

Gly Pro Glu Gly Pro Glu Gly Pro Gln Gly Pro Glu
            195                 200

Gly Pro Glu Gly Pro Glu Gly Pro Glu Gly Pro Gln
205                     210                     215

Gly Pro Glu Gly Pro Glu Gly Pro Glu Gly Pro Glu
                220                 225

Gly Pro Gln Gly Pro Glu Gly Pro Glu Gly Pro Glu
        230             235                     240

Gly Pro Glu Gly Pro Gln Gly Pro Glu Gly Pro Glu
                245                     250

Gly Pro Glu Gly Pro Glu Gly Pro Gln Gly Pro Glu
            255                 260

Gly Pro Glu Gly Pro Glu Gly Pro Glu
265                     270

( 2 ) INFORMATION FOR SEQ ID NO:4:

( i ) SEQUENCE CHARACTERISTICS:
        ( A ) LENGTH: 30
        ( B ) TYPE: Amino acid
        ( D ) TOPOLOGY: Linear ( i i ) MOLECULE TYPE: Polypeptide ( i i i ) HYPOTHETICAL: No ( i v ) ANTI-SENSE: No ( v ) FRAGMENT TYPE: Internal ( v i ) ORIGINAL SOURCE: Synthetically prepared ( v i i ) IMMEDIATE SOURCE: Synthetically prepared ( x ) PUBLICATION INFORMATION: None ( x i ) SEQUENCE DESCRIPTION: SEQ ID NO:4:

Gly Pro Gln Gly Pro Glu Gly Pro Glu Gly Pro Glu
                  5                      10

Gly Pro Glu Gly Pro Gln Gly Pro Glu Gly Pro Glu
            15                     20

Gly Pro Glu Gly Pro Glu
25                30

(2) INFORMATION FOR SEQ ID NO:5:

(i) SEQUENCE CHARACTERISTICS:
       (A) LENGTH: 540
       (B) TYPE: Amino acid
       (D) TOPOLOGY: Linear (ii) MOLECULE TYPE: Polypeptide (iii) HYPOTHETICAL: No (iv) ANTI-SENSE: No (v) FRAGMENT TYPE: C-terminal (vi) ORIGINAL SOURCE: Saccharomyces
              cerevisiae (vii) IMMEDIATE SOURCE: Saccharomyces
              cerevisiae (x) PUBLICATION INFORMATION: None (xi) SEQUENCE DESCRIPTION: SEQ ID NO:5:

Gly Pro Gln Gly Pro Glu Gly Pro Glu Gly Pro Glu
                  5                      10

Gly Pro Glu Gly Pro Gln Gly Pro Glu Gly Pro Glu
            15                     20

Gly Pro Glu Gly Pro Glu Gly Pro Gln Gly Pro Glu
25                30                       35

Gly Pro Glu Gly Pro Glu Gly Pro Glu Gly Pro Gln
            40                     45

Gly Pro Glu Gly Pro Glu Gly Pro Glu Gly Pro Glu
      50                55                    60

Gly Pro Gln Gly Pro Glu Gly Pro Glu Gly Pro Glu
                  65                     70

Gly Pro Glu Gly Pro Gln Gly Pro Glu Gly Pro Glu
            75                     80

Gly Pro Glu Gly Pro Glu Gly Pro Gln Gly Pro Glu
85                90                       95

Gly Pro Glu Gly Pro Glu Gly Pro Glu Gly Pro Gln
            100                    105

Gly Pro Glu Gly Pro Glu Gly Pro Glu Gly Pro Glu
      110               115                   120

Gly Pro Gln Gly Pro Glu Gly Pro Glu Gly Pro Glu
                  125                    130

Gly Pro Glu Gly Pro Gln Gly Pro Glu Gly Pro Glu
            135                    140

Gly Pro Glu Gly Pro Glu Gly Pro Gln Gly Pro Glu
145               150                       155

Gly Pro Glu Gly Pro Glu Gly Pro Glu Gly Pro Gln
            160                    165

Gly Pro Glu Gly Pro Glu Gly Pro Glu Gly Pro Glu
      170               175                   180

-continued

```
Gly Pro Gln Gly Pro Glu Gly Pro Glu Gly Pro Glu
            185             190
Gly Pro Glu Gly Pro Gln Gly Pro Glu Gly Pro Glu
            195             200
Gly Pro Glu Gly Pro Glu Gly Pro Gln Gly Pro Glu
205                 210             215
Gly Pro Glu Gly Pro Glu Gly Pro Glu Gly Pro Gln
            220             225
Gly Pro Glu Gly Pro Glu Gly Pro Glu Gly Pro Glu
            230     235                     240
Gly Pro Gln Gly Pro Glu Gly Pro Glu Gly Pro Glu
            245             250
Gly Pro Glu Gly Pro Gln Gly Pro Glu Gly Pro Glu
            255             260
Gly Pro Glu Gly Pro Glu Gly Pro Glu Gly Pro Glu
265                 270             275
Gly Pro Glu Gly Pro Glu Gly Pro Glu Gly Pro Gln
            280             285
Gly Pro Glu Gly Pro Glu Gly Pro Glu Gly Pro Glu
            290     295                     300
Gly Pro Gln Gly Pro Glu Gly Pro Glu Gly Pro Glu
            305             310
Gly Pro Glu Gly Pro Gln Gly Pro Glu Gly Pro Glu
            315             320
Gly Pro Glu Gly Pro Glu Gly Pro Glu Gly Pro Glu
325                 330             335
Gly Pro Glu Gly Pro Glu Gly Pro Glu Gly Pro Gln
            340             345
Gly Pro Glu Gly Pro Glu Gly Pro Glu Gly Pro Glu
            350     355                     360
Gly Pro Gln Gly Pro Glu Gly Pro Glu Gly Pro Glu
            365             370
Gly Pro Glu Gly Pro Gln Gly Pro Glu Gly Pro Glu
            375             380
Gly Pro Glu Gly Pro Glu Gly Pro Gln Gly Pro Glu
385                 390             395
Gly Pro Glu Gly Pro Glu Gly Pro Glu Gly Pro Glu
            400             405
Gly Pro Glu Gly Pro Glu Gly Pro Glu Gly Pro Glu
            410     415                     420
Gly Pro Gln Gly Pro Glu Gly Pro Glu Gly Pro Glu
            425             430
Gly Pro Glu Gly Pro Gln Gly Pro Glu Gly Pro Glu
            435             440
Gly Pro Glu Gly Pro Glu Gly Pro Gln Gly Pro Glu
445                 450                     455
Gly Pro Glu Gly Pro Glu Gly Pro Glu Gly Pro Gln
            460             465
Gly Pro Glu Gly Pro Glu Gly Pro Glu Gly Pro Glu
            470     475                     480
Gly Pro Gln Gly Pro Glu Gly Pro Glu Gly Pro Glu
            485             490
Gly Pro Glu Gly Pro Gln Gly Pro Glu Gly Pro Glu
            495             500
```

| Gly | Pro | Glu | Gly | Pro | Glu | Gly | Pro | Gln | Gly | Pro | Glu |
|-----|-----|-----|-----|-----|-----|-----|-----|-----|-----|-----|-----|
| 505 |     |     |     |     | 510 |     |     |     | 515 |     |     |

| Gly | Pro | Glu | Gly | Pro | Glu | Gly | Pro | Glu | Gly | Pro | Gln |
|-----|-----|-----|-----|-----|-----|-----|-----|-----|-----|-----|-----|
|     |     |     |     | 520 |     |     |     | 525 |     |     |     |

| Gly | Pro | Glu | Gly | Pro | Glu | Gly | Pro | Glu | Gly | Pro | Glu |
|-----|-----|-----|-----|-----|-----|-----|-----|-----|-----|-----|-----|
|     |     | 530 |     |     |     | 535 |     |     |     |     | 540 |

( 2 ) INFORMATION FOR SEQ ID NO:6:

( i ) SEQUENCE CHARACTERISTICS:
        ( A ) LENGTH: 25
        ( B ) TYPE: Amino acid
        ( D ) TOPOLOGY: Linear ( i i ) MOLECULE TYPE: Polypeptide ( i i i ) HYPOTHETICAL: No ( i v ) ANTI-SENSE: No ( v ) FRAGMENT TYPE: Internal ( v i ) ORIGINAL SOURCE: Synthetically prepared ( v i i ) IMMEDIATE SOURCE: Synthetically
            prepared ( x ) PUBLICATION INFORMATION: None ( x i ) SEQUENCE DESCRIPTION: SEQ ID NO:6:

| Gly | Pro | Ile | Gly | Leu | Ile | Gly | Pro | Arg | Gly | Pro | Pro |
|-----|-----|-----|-----|-----|-----|-----|-----|-----|-----|-----|-----|
|     |     |     |     | 5   |     |     |     |     | 10  |     |     |

| Gly | Ala | Ser | Gly | Ala | Pro | Gly | Pro | Glu | Gly | Phe | Gln |
|-----|-----|-----|-----|-----|-----|-----|-----|-----|-----|-----|-----|
|     |     |     | 15  |     |     |     |     | 20  |     |     |     |

Gly
25

( 2 ) INFORMATION FOR SEQ ID NO:7:

( i ) SEQUENCE CHARACTERISTICS:
        ( A ) LENGTH: 25
        ( B ) TYPE: Amino acid
        ( D ) TOPOLOGY: Linear ( i i ) MOLECULE TYPE: Polypeptide ( i i i ) HYPOTHETICAL: No ( i v ) ANTI-SENSE: No ( v ) FRAGMENT TYPE: Internal ( v i ) ORIGINAL SOURCE: Synthetically prepared ( v i i ) IMMEDIATE SOURCE: Synthetically
            prepared ( x ) PUBLICATION INFORMATION: None ( x i ) SEQUENCE DESCRIPTION: SEQ ID NO:7:

| Gly | Pro | Lys | Gly | Leu | Lys | Gly | Pro | Arg | Gly | Pro | Pro |
|-----|-----|-----|-----|-----|-----|-----|-----|-----|-----|-----|-----|
|     |     |     |     | 5   |     |     |     |     | 10  |     |     |

| Gly | Ala | Ser | Gly | Ala | Pro | Gly | Pro | Glu | Gly | Phe | Gln |
|-----|-----|-----|-----|-----|-----|-----|-----|-----|-----|-----|-----|
|     |     |     | 15  |     |     |     |     | 20  |     |     |     |

Gly
25

( 2 ) INFORMATION FOR SEQ ID NO:8:

( i ) SEQUENCE CHARACTERISTICS:
    ( A ) LENGTH: 25
    ( B ) TYPE: Amino acid
    ( D ) TOPOLOGY: Linear ( i i ) MOLECULE TYPE: Polypeptide ( i i i ) HYPOTHETICAL: No ( i v ) ANTI-SENSE: No ( v ) FRAGMENT TYPE: Internal ( v i ) ORIGINAL SOURCE: Synthetically prepared ( v i i ) IMMEDIATE SOURCE: Synthetically prepared ( x ) PUBLICATION INFORMATION: None ( x i ) SEQUENCE DESCRIPTION: SEQ ID NO:8:

Gly Pro Asn Gly Leu Asn Gly Pro Arg Gly Pro Pro
                      5                         10

Gly Ala Ser Gly Ala Pro Gly Pro Glu Gly Phe Gln
            15                         20

Gly
25

( 2 ) INFORMATION FOR SEQ ID NO:9:

( i ) SEQUENCE CHARACTERISTICS:
    ( A ) LENGTH: 25
    ( B ) TYPE: Amino acid
    ( D ) TOPOLOGY: Linear ( i i ) MOLECULE TYPE: Polypeptide ( i i i ) HYPOTHETICAL: No ( i v ) ANTI-SENSE: No ( v ) FRAGMENT TYPE: Internal ( v i ) ORIGINAL SOURCE: Synthetically prepared ( v i i ) IMMEDIATE SOURCE: Synthetically prepared ( x ) PUBLICATION INFORMATION: None ( x i ) SEQUENCE DESCRIPTION: SEQ ID NO:9:

Gly Pro Tyr Gly Leu Tyr Gly Pro Arg Gly Pro Pro
                      5                         10

Gly Ala Ser Gly Ala Pro Gly Pro Glu Gly Phe Gln
            15                         20

Gly
25

( 2 ) INFORMATION FOR SEQ ID NO:10:

( i ) SEQUENCE CHARACTERISTICS:
    ( A ) LENGTH: 25
    ( B ) TYPE: Amino acid
    ( D ) TOPOLOGY: Linear ( i i ) MOLECULE TYPE: Polypeptide ( i i i ) HYPOTHETICAL: No ( i v ) ANTI-SENSE: No ( v ) FRAGMENT TYPE: Internal ( v i ) ORIGINAL SOURCE: Synthetically prepared ( v i i ) IMMEDIATE SOURCE: Synthetically prepared ( x ) PUBLICATION INFORMATION: None ( x i ) SEQUENCE DESCRIPTION: SEQ ID NO:10:

Gly Pro Gln Gly Leu Gln Gly Pro Arg Gly Pro Pro
                  5                   10
Gly Ala Ser Gly Ala Pro Gly Pro Glu Gly Phe Gln
         15                  20
Gly
 25

( 2 ) INFORMATION FOR SEQ ID NO:11:

( i ) SEQUENCE CHARACTERISTICS:
( A ) LENGTH: 25
( B ) TYPE: Amino acid
( D ) TOPOLOGY: Linear ( i i ) MOLECULE TYPE: Polypeptide ( i i i ) HYPOTHETICAL: No ( i v ) ANTI-SENSE: No ( v ) FRAGMENT TYPE: Internal ( v i ) ORIGINAL SOURCE: Synthetically prepared ( v i i ) IMMEDIATE SOURCE: Synthetically prepared ( x ) PUBLICATION INFORMATION: None ( x i ) SEQUENCE DESCRIPTION: SEQ ID NO:11:

Gly Pro Met Gly Leu Met Gly Pro Arg Gly Pro Pro
                  5                   10
Gly Ala Ser Gly Ala Pro Gly Pro Glu Gly Phe Gln
         15                  20
Gly
 25

( 2 ) INFORMATION FOR SEQ ID NO:12:

( i ) SEQUENCE CHARACTERISTICS:
( A ) LENGTH: 25
( B ) TYPE: Amino acid
( D ) TOPOLOGY: Linear ( i i ) MOLECULE TYPE: Polypeptide ( i i i ) HYPOTHETICAL: No ( i v ) ANTI-SENSE: No ( v ) FRAGMENT TYPE: Internal ( v i ) ORIGINAL SOURCE: Synthetically prepared ( v i i ) IMMEDIATE SOURCE: Synthetically prepared ( x ) PUBLICATION INFORMATION: None ( x i ) SEQUENCE DESCRIPTION: SEQ ID NO:12:

Gly Pro His Gly Leu His Gly Pro Arg Gly Pro Pro

```
                              5              10
Gly Ala Ser Gly Ala Pro Gly Pro Glu Gly Phe Gln
            15                  20

Gly
25
```

( 2 ) INFORMATION FOR SEQ ID NO:13:

( i ) SEQUENCE CHARACTERISTICS:
        ( A ) LENGTH: 25
        ( B ) TYPE: Amino acid
        ( D ) TOPOLOGY: Linear ( i i ) MOLECULE TYPE: Polypeptide ( i i i ) HYPOTHETICAL: No ( i v ) ANTI-SENSE: No ( v ) FRAGMENT TYPE: Internal ( v i ) ORIGINAL SOURCE: Synthetically prepared ( v i i ) IMMEDIATE SOURCE: Synthetically prepared ( x ) PUBLICATION INFORMATION: None ( x i ) SEQUENCE DESCRIPTION: SEQ ID NO:13:

```
Gly Pro Ile Gly Leu Met Gly Pro Arg Gly Pro Pro
                5                  10

Gly Ala Ser Gly Ala Pro Gly Pro Glu Gly Phe Gln
            15                  20

Gly
25
```

( 2 ) INFORMATION FOR SEQ ID NO:14:

( i ) SEQUENCE CHARACTERISTICS:
        ( A ) LENGTH: 25
        ( B ) TYPE: Amino acid
        ( D ) TOPOLOGY: Linear ( i i ) MOLECULE TYPE: Polypeptide ( i i i ) HYPOTHETICAL: No ( i v ) ANTI-SENSE: No ( v ) FRAGMENT TYPE: Internal ( v i ) ORIGINAL SOURCE: Synthetically prepared ( v i i ) IMMEDIATE SOURCE: Synthetically prepared ( x ) PUBLICATION INFORMATION: None ( x i ) SEQUENCE DESCRIPTION: SEQ ID NO:14:

```
Gly Pro Met Gly Leu Ile Gly Pro Arg Gly Pro Pro
                5                  10

Gly Ala Ser Gly Ala Pro Gly Pro Glu Gly Phe Gln
            15                  20

Gly
25
```

( 2 ) INFORMATION FOR SEQ ID NO:15:

( i ) SEQUENCE CHARACTERISTICS:

(A) LENGTH: 270
(B) TYPE: Amino acid
(D) TOPOLOGY: Linear (ii) MOLECULE TYPE: Polypeptide (iii) HYPOTHETICAL: No (iv) ANTI-SENSE: No (v) FRAGMENT TYPE: Internal (vi) ORIGINAL SOURCE: Saccharomyces
    cerevisiae (vii) IMMEDIATE SOURCE: Saccharomyces
    cerevisiae (x) PUBLICATION INFORMATION: None (xi) SEQUENCE DESCRIPTION: SEQ ID NO:15:

```
Gly Pro Gln Gly Pro Glu Gly Pro Glu Gly Pro Glu
                  5                10

Gly Pro Glu Gly Pro Gln Gly Pro Glu Gly Pro Glu
             15                 20

Gly Pro Glu Gly Pro Glu Gly Pro Gln Gly Pro Glu
 25               30                     35

Gly Pro Glu Gly Pro Glu Gly Pro Glu Gly Pro Gln
             40                 45

Gly Pro Glu Gly Pro Glu Gly Pro Glu Gly Pro Glu
     50              55                      60

Gly Pro Gln Gly Pro Glu Gly Pro Glu Gly Pro Glu
                 65                 70

Gly Pro Glu Gly Pro Gln Gly Pro Glu Gly Pro Glu
 75              80

Gly Pro Glu Gly Pro Glu Gly Pro Gln Gly Pro Glu
 85              90                     95

Gly Pro Glu Gly Pro Glu Gly Pro Glu Gly Pro Gln
100              105

Gly Pro Glu Gly Pro Glu Gly Pro Glu Gly Pro Glu
110              115                    120

Gly Pro Gln Gly Pro Glu Gly Pro Glu Gly Pro Glu
125              130

Gly Pro Glu Gly Pro Gln Gly Pro Glu Gly Pro Glu
135              140

Gly Pro Glu Gly Pro Glu Gly Pro Gln Gly Pro Glu
145              150                    155

Gly Pro Glu Gly Pro Glu Gly Pro Glu Gly Pro Gln
160              165

Gly Pro Glu Gly Pro Glu Gly Pro Glu Gly Pro Glu
170              175                    180

Gly Pro Gln Gly Pro Glu Gly Pro Glu Gly Pro Glu
185              190

Gly Pro Glu Gly Pro Gln Gly Pro Glu Gly Pro Glu
195              200

Gly Pro Glu Gly Pro Glu Gly Pro Gln Gly Pro Glu
205              210                    215

Gly Pro Glu Gly Pro Glu Gly Pro Glu Gly Pro Gln
220              225

Gly Pro Glu Gly Pro Glu Gly Pro Glu Gly Pro Glu
```

```
                                 235                         240
230

Gly Pro Gln Gly Pro Glu Gly Pro Glu Gly Pro Glu
245                     250

Gly Pro Glu Gly Pro Gln Gly Pro Glu Gly Pro Glu
255                     260

Gly Pro Glu Gly Pro Glu
265                     270
```

( 2 ) INFORMATION FOR SEQ ID NO:16:

( i ) SEQUENCE CHARACTERISTICS:
        ( A ) LENGTH: 543
        ( B ) TYPE: Amino acid
        ( D ) TOPOLOGY: Linear ( i i ) MOLECULE TYPE: Polypeptide ( i i i ) HYPOTHETICAL: No ( i v ) ANTI-SENSE: No ( v ) FRAGMENT TYPE: C-terminal ( v i ) ORIGINAL SOURCE: Saccharomyces
                   cerevisiae ( v i i ) IMMEDIATE SOURCE: Saccharomyces
                   cerevisiae ( x ) PUBLICATION INFORMATION: None ( x i ) SEQUENCE DESCRIPTION: SEQ ID NO:16:

```
Gly Pro Glu Gly Pro Gln Gly Pro Glu Gly Pro Glu
                5                       10

Gly Pro Glu Gly Pro Glu Gly Pro Gln Gly Pro Glu
            15                      20

Gly Pro Glu Gly Pro Glu Gly Pro Glu Gly Pro Gln
25                      30                      35

Gly Pro Glu Gly Pro Glu Gly Pro Glu Gly Pro Glu
            40                      45

Gly Pro Gln Gly Pro Glu Gly Pro Glu Gly Pro Glu
50                      55                      60

Gly Pro Glu Gly Pro Gln Gly Pro Glu Gly Pro Glu
            65                      70

Gly Pro Glu Gly Pro Glu Gly Pro Gln Gly Pro Glu
            75                      80

Gly Pro Glu Gly Pro Glu Gly Pro Glu Gly Pro Gln
85                      90                      95

Gly Pro Glu Gly Pro Glu Gly Pro Glu Gly Pro Glu
            100                     105

Gly Pro Gln Gly Pro Glu Gly Pro Glu Gly Pro Glu
    110                     115                 120

Gly Pro Glu Gly Pro Gln Gly Pro Glu Gly Pro Glu
            125                     130

Gly Pro Glu Gly Pro Glu Gly Pro Gln Gly Pro Glu
            135                     140

Gly Pro Glu Gly Pro Glu Gly Pro Glu Gly Pro Gln
145                     150                     155

Gly Pro Glu Gly Pro Glu Gly Pro Glu Gly Pro Glu
            160                     165

Gly Pro Gln Gly Pro Glu Gly Pro Glu Gly Pro Glu
```

|     |     |     |     |     |     |     |     |     |     |     |
| --- | --- | --- | --- | --- | --- | --- | --- | --- | --- | --- |
|     | 170 |     |     |     | 175 |     |     |     | 180 |     |
| Gly | Pro | Glu | Gly | Pro | Gln | Gly | Pro | Glu | Gly | Pro | Glu
|     |     |     |     | 185 |     |     |     | 190 |     |     |
| Gly | Pro | Glu | Gly | Pro | Glu | Gly | Pro | Gln | Gly | Pro | Glu
|     |     | 195 |     |     |     | 200 |     |     |     |     |
| Gly | Pro | Glu | Gly | Pro | Glu | Gly | Pro | Glu | Gly | Pro | Gln
| 205 |     |     |     | 210 |     |     |     | 215 |     |     |
| Gly | Pro | Glu | Gly | Pro | Glu | Gly | Pro | Glu | Gly | Pro | Glu
|     |     |     | 220 |     |     |     | 225 |     |     |     |
| Gly | Pro | Gln | Gly | Pro | Glu | Gly | Pro | Glu | Gly | Pro | Glu
|     |     | 230 |     |     |     | 235 |     |     |     | 240 |
| Gly | Pro | Glu | Gly | Pro | Gln | Gly | Pro | Glu | Gly | Pro | Glu
|     |     |     |     | 245 |     |     |     | 250 |     |     |
| Gly | Pro | Glu | Gly | Pro | Glu | Gly | Pro | Gln | Gly | Pro | Glu
|     |     | 255 |     |     |     | 260 |     |     |     |     |
| Gly | Pro | Glu | Gly | Pro | Glu | Gly | Pro | Glu | Gly | Pro | Gln
| 265 |     |     |     | 270 |     |     |     | 275 |     |     |
| Gly | Pro | Glu | Gly | Pro | Glu | Gly | Pro | Glu | Gly | Pro | Glu
|     |     |     | 280 |     |     |     | 285 |     |     |     |
| Gly | Pro | Gln | Gly | Pro | Glu | Gly | Pro | Glu | Gly | Pro | Glu
|     |     | 290 |     |     |     | 295 |     |     |     | 300 |
| Gly | Pro | Glu | Gly | Pro | Gln | Gly | Pro | Glu | Gly | Pro | Glu
|     |     |     |     | 305 |     |     |     | 310 |     |     |
| Gly | Pro | Glu | Gly | Pro | Glu | Gly | Pro | Gln | Gly | Pro | Glu
|     |     | 315 |     |     |     | 320 |     |     |     |     |
| Gly | Pro | Glu | Gly | Pro | Glu | Gly | Pro | Glu | Gly | Pro | Gln
| 325 |     |     |     | 330 |     |     |     | 335 |     |     |
| Gly | Pro | Glu | Gly | Pro | Glu | Gly | Pro | Glu | Gly | Pro | Glu
|     |     |     | 340 |     |     |     | 345 |     |     |     |
| Gly | Pro | Gln | Gly | Pro | Glu | Gly | Pro | Glu | Gly | Pro | Glu
|     |     | 350 |     |     |     | 355 |     |     |     | 360 |
| Gly | Pro | Glu | Gly | Pro | Gln | Gly | Pro | Glu | Gly | Pro | Glu
|     |     |     |     | 365 |     |     |     | 370 |     |     |
| Gly | Pro | Glu | Gly | Pro | Glu | Gly | Pro | Gln | Gly | Pro | Glu
|     |     | 375 |     |     |     | 380 |     |     |     |     |
| Gly | Pro | Glu | Gly | Pro | Glu | Gly | Pro | Glu | Gly | Pro | Gln
| 385 |     |     |     | 390 |     |     |     | 395 |     |     |
| Gly | Pro | Glu | Gly | Pro | Glu | Gly | Pro | Glu | Gly | Pro | Glu
|     |     |     | 400 |     |     |     | 405 |     |     |     |
| Gly | Pro | Gln | Gly | Pro | Glu | Gly | Pro | Glu | Gly | Pro | Glu
|     |     | 410 |     |     |     | 415 |     |     |     | 420 |
| Gly | Pro | Glu | Gly | Pro | Gln | Gly | Pro | Glu | Gly | Pro | Glu
|     |     |     |     | 425 |     |     |     | 430 |     |     |
| Gly | Pro | Glu | Gly | Pro | Glu | Gly | Pro | Gln | Gly | Pro | Glu
|     |     | 435 |     |     |     | 440 |     |     |     |     |
| Gly | Pro | Glu | Gly | Pro | Glu | Gly | Pro | Glu | Gly | Pro | Gln
| 445 |     |     |     | 450 |     |     |     | 455 |     |     |
| Gly | Pro | Glu | Gly | Pro | Glu | Gly | Pro | Glu | Gly | Pro | Glu
|     |     |     | 460 |     |     |     | 465 |     |     |     |
| Gly | Pro | Gln | Gly | Pro | Glu | Gly | Pro | Glu | Gly | Pro | Glu
|     |     | 470 |     |     |     | 475 |     |     |     | 480 |
| Gly | Pro | Glu | Gly | Pro | Gln | Gly | Pro | Glu | Gly | Pro | Glu
|     |     |     |     | 485 |     |     |     | 490 |     |     |

| Gly | Pro | Glu<br>495 | Gly | Pro | Glu | Gly | Pro | Gln<br>500 | Gly | Pro | Glu |

| Gly<br>505 | Pro | Glu | Gly | Pro | Glu<br>510 | Gly | Pro | Glu | Gly | Pro | Gln<br>515 |

| Gly | Pro | Glu | Gly<br>520 | Pro | Glu | Gly | Pro | Glu<br>525 | Gly | Pro | Glu |

| Gly | Pro | Gln<br>530 | Gly | Pro | Glu | Gly<br>535 | Pro | Glu | Gly | Pro | Glu<br>540 |

Gly Pro Glu ( 2 ) INFORMATION FOR SEQ ID NO:17:

( i ) SEQUENCE CHARACTERISTICS:
        ( A ) LENGTH: 109 nucleotides
        ( B ) TYPE: Nucleic acid
        ( C ) STRANDEDNESS: Single
        ( D ) TOPOLOGY: Linear ( i i ) MOLECULE TYPE: Encoding DNA strand ( i i i ) HYPOTHETICAL: No ( i v ) ANTI-SENSE: No ( v i ) ORIGINAL SOURCE: Synthetically prepared ( v i i ) IMMEDIATE SOURCE: Synthetically prepared ( x ) PUBLICATION INFORMATION: None ( x i ) SEQUENCE DESCRIPTION: SEQ ID NO:17:

| AATTCGGTCC | CGAGGGTCCA | CAAGGTCCAG | AAGGTCCAGA | 40 |
| GGTCCAGAA | GGTCCAGAAG | GTCCACAAGG | TCCAGAAGGT | 80 |
| CCAGAAGGTC | CAGAAGGTCC | CGAGCTAAG | | 109 |

( 2 ) INFORMATION FOR SEQ ID NO:18:

( i ) SEQUENCE CHARACTERISTICS:
        ( A ) LENGTH: 109 nucleotides
        ( B ) TYPE: Nucleic acid
        ( C ) STRANDEDNESS: Single
        ( D ) TOPOLOGY: Linear ( i i ) MOLECULE TYPE: Encoding DNA strand ( i i i ) HYPOTHETICAL: No ( i v ) ANTI-SENSE: No ( v i ) ORIGINAL SOURCE: Synthetically prepared ( v i i ) IMMEDIATE SOURCE: Synthetically prepared ( x ) PUBLICATION INFORMATION: None ( x i ) SEQUENCE DESCRIPTION: SEQ ID NO:18:

| TCGACTTAGC | TCGGGACCTT | CTGGACCTTC | TGGACCTTCT | 40 |
| GGACCTTGTG | GACCTTCTGG | ACCTTCTGGA | CCTTCTGGAC | 80 |
| CTTCTGGACC | TTGTGGACCC | TCGGGACCG | | 109 |

( 2 ) INFORMATION FOR SEQ ID NO:19:

( i ) SEQUENCE CHARACTERISTICS:
        ( A ) LENGTH: 105

(B) TYPE: Amino acid
(D) TOPOLOGY: Linear (ii) MOLECULE TYPE: Polypeptide (iii) HYPOTHETICAL: No (iv) ANTI-SENSE: No (v) FRAGMENT TYPE: C-terminal (vi) ORIGINAL SOURCE: Saccharomyces
     cerevisiae (vii) IMMEDIATE SOURCE: Saccharomyces
      cerevisiae (x) PUBLICATION INFORMATION: None (xi) SEQUENCE DESCRIPTION: SEQ ID NO:19:

```
Asp Tyr Lys Asp Asp Asp Lys Glu Phe Gly Lys
                  5                10

Gly Pro Glu Gly Pro Gln Gly Pro Glu
             15              20

Gly Pro Glu Gly Pro Glu Gly Pro Glu Gly Pro Gln
             25              30

Gly Pro Glu Gly Pro Glu Gly Pro Glu Gly Pro Glu
    35                   40                    45

Gly Pro Gln Gly Pro Glu Gly Pro Glu Gly Pro Glu
             50                   55

Gly Pro Glu Gly Pro Gln Gly Pro Glu Gly Pro Glu
        60                   65

Gly Pro Glu Gly Pro Glu Gly Pro Gln Gly Pro Glu
70                       75                   80

Gly Pro Glu Gly Pro Glu Gly Pro Glu Gly Pro Gln
             85                   90

Gly Pro Glu Gly Pro Glu Gly Pro Glu Gly Pro Glu
        95               100                  105
```

(2) INFORMATION FOR SEQ ID NO:20:

(i) SEQUENCE CHARACTERISTICS:
    (A) LENGTH: 285
    (B) TYPE: Amino acid
    (D) TOPOLOGY: Linear (ii) MOLECULE TYPE: Polypeptide (iii) HYPOTHETICAL: No (iv) ANTI-SENSE: No (v) FRAGMENT TYPE: C-terminal (vi) ORIGINAL SOURCE: Saccharomyces
     cerevisiae (vii) IMMEDIATE SOURCE: Saccharomyces
      cerevisiae (x) PUBLICATION INFORMATION: None (xi) SEQUENCE DESCRIPTION: SEQ ID NO:20:

```
Asp Tyr Lys Asp Asp Asp Lys Glu Phe Gly Lys
                  5                10

Gly Pro Glu Gly Pro Gln Gly Pro Glu Gly Pro Glu
             15                   20
```

-continued

| | | | | | | | | | | | |
|---|---|---|---|---|---|---|---|---|---|---|---|
| Gly | Pro | Glu | Gly | Pro | Glu | Gly | Pro | Gln | Gly | Pro | Glu |
| 25 | | | | | 30 | | | | | 35 | |
| Gly | Pro | Glu | Gly | Pro | Glu | Gly | Pro | Glu | Gly | Pro | Gln |
| | | | 40 | | | | | 45 | | | |
| Gly | Pro | Glu | Gly | Pro | Glu | Gly | Pro | Glu | Gly | Pro | Glu |
| | | 50 | | | | 55 | | | | | 60 |
| Gly | Pro | Gln | Gly | Pro | Glu | Gly | Pro | Glu | Gly | Pro | Glu |
| | | | | 65 | | | | | 70 | | |
| Gly | Pro | Glu | Gly | Pro | Gln | Gly | Pro | Glu | Gly | Pro | Glu |
| | | 75 | | | | | | 80 | | | |
| Gly | Pro | Glu | Gly | Pro | Glu | Gly | Pro | Gln | Gly | Pro | Glu |
| 85 | | | | | 90 | | | | | 95 | |
| Gly | Pro | Glu | Gly | Pro | Glu | Gly | Pro | Glu | Gly | Pro | Gln |
| | | | 100 | | | | | 105 | | | |
| Gly | Pro | Glu | Gly | Pro | Glu | Gly | Pro | Glu | Gly | Pro | Glu |
| | | 110 | | | | 115 | | | | | 120 |
| Gly | Pro | Gln | Gly | Pro | Glu | Gly | Pro | Glu | Gly | Pro | Glu |
| | | | | 125 | | | | | 130 | | |
| Gly | Pro | Glu | Gly | Pro | Gln | Gly | Pro | Glu | Gly | Pro | Glu |
| | | 135 | | | | | | 140 | | | |
| Gly | Pro | Glu | Gly | Pro | Glu | Gly | Pro | Gln | Gly | Pro | Glu |
| 145 | | | | | 150 | | | | | 155 | |
| Gly | Pro | Glu | Gly | Pro | Glu | Gly | Pro | Glu | Gly | Pro | Gln |
| | | | 160 | | | | | 165 | | | |
| Gly | Pro | Glu | Gly | Pro | Glu | Gly | Pro | Glu | Gly | Pro | Glu |
| | | 170 | | | | 175 | | | | | 180 |
| Gly | Pro | Gln | Gly | Pro | Glu | Gly | Pro | Glu | Gly | Pro | Glu |
| | | | | 185 | | | | | 190 | | |
| Gly | Pro | Glu | Gly | Pro | Gln | Gly | Pro | Glu | Gly | Pro | Glu |
| | | 195 | | | | | | 200 | | | |
| Gly | Pro | Glu | Gly | Pro | Glu | Gly | Pro | Gln | Gly | Pro | Glu |
| 205 | | | | | 210 | | | | | 215 | |
| Gly | Pro | Glu | Gly | Pro | Glu | Gly | Pro | Glu | Gly | Pro | Gln |
| | | | 220 | | | | | 225 | | | |
| Gly | Pro | Glu | Gly | Pro | Glu | Gly | Pro | Glu | Gly | Pro | Glu |
| | | 230 | | | | 235 | | | | | 240 |
| Gly | Pro | Gln | Gly | Pro | Glu | Gly | Pro | Glu | Gly | Pro | Glu |
| | | | | 245 | | | | | 250 | | |
| Gly | Pro | Glu | Gly | Pro | Gln | Gly | Pro | Glu | Gly | Pro | Glu |
| | | 255 | | | | | | 260 | | | |
| Gly | Pro | Glu | Gly | Pro | Glu | Gly | Pro | Gln | Gly | Pro | Glu |
| 265 | | | | | 270 | | | | | 275 | |
| Gly | Pro | Glu | Gly | Pro | Glu | Gly | Pro | Glu | | | |
| | | | 280 | | | | | 285 | | | |

SILVER HALIDE EMULSIONS, ELEMENTS AND METHODS OF MAKING SAME USING SYNTHETIC BIOPOLYMER PEPTIZERS

FIELD OF THE INVENTION

The present invention relates in general to photography and in particular to the preparation of silver halide emulsions and elements useful in photography. More specifically, it relates to the use of certain synthetic biopolymers as peptizers in the preparation of silver halide emulsions to control grain morphology.

BACKGROUND OF THE INVENTION

It is well known that silver halide emulsion preparation includes the stages of nucleation and growth of the silver halide grains within a continuous phase. In the nucleation stage, new grains of very small size are created. The growth stage involves addition of new material to the existing small grains to make them larger.

Both the nucleation and growth stages of silver halide emulsion preparation require the use of a peptizer to avoid the coalescence or flocculation of the silver halide grains and to control grain growth and dispersity. The coated emulsion contains a vehicle that typically includes a colloidal binder (or mixtures of binders) and the peptizer. Characteristics of grain growth and dispersity have a critical effect on sensitometric and photographic properties of the resulting emulsions.

While a variety of hydrophilic colloids are known to be useful as peptizers, the most commonly employed peptizers are gelatins, such as alkali-treated gelatin (bovine bone or hide gelatin) or acid-treated gelatin (pigskin or bovine bone gelatin), and gelatin derivatives, such as acetylated and phthalated gelatins. Such peptizers are collectively known as "gelatino-peptizers".

These same materials can also be used as the binders in the photographic emulsions. However, there are many similar materials that are useful as binders but which are ineffective as peptizers.

Gelatins generally contain various impurities and comprise a wide variety of different types of protein and polypeptide molecules in various configurations and sizes. The resulting lack of uniformity from batch to batch has been a recognized problem for a long time, and various researchers have valiantly attempted to modify or replace gelatins to provide more uniform peptizers or binders. Removal of impurities by various means is a common practice in order to produce photographically acceptable gelatins.

Synthetic copolymers containing sulfide groups have been prepared to replace gelatin as a peptizer (see U.S. Pat. No. 3,615,624 of Smith et al). Synthetic gelatin replacements have also been prepared as polyimide condensation products of methionine and an α-amino carboxylic acid (see U.S. Pat. No. 4,315,072 of Fox et al).

Naturally occurring gelatins have been treated in a variety of ways to modify its peptizing and sensitometric properties. For example, U.S. Pat. No. 4,713,320 (Maskasky) describes lowering the content of methionine in the gelatin by oxidation in order to make thin tabular silver halide grains having certain characteristics. Alkylation of methionine groups in gelatin is described in U.S. Pat. No. 4,942,120 (King et al) for similar purposes. Use of gelatin with low cysteine content is described in U.S. Pat. No. 4,990,440 (Moll et al).

More recently, polypeptides made by recombinant DNA techniques are described as coating vehicle replacements for type I collagen of conventional gelatin for use in holography (see FR-A-2,685,347, Obrecht et al). The described polypeptides were expressed in *E. coli* and recovered using conventional techniques and nickel-NTA-agarose resins. The noted polypeptides have specific amino acid characteristics. The specific peptides are rich in Gly-Pro-Ala and Gly-Glu-Arg triplets, and also contain a triplet of histidines to provide affinity for the capture resins. A methionine is included between the histidine and non-histidine triplets to enable chemical degradation with cyanogen bromide and release of the desired polypeptide. A cysteine is included for binding to chromatographic resins or proteins, and a leucine is placed critically between the methionine and histidine because of its restriction site. Thus, the polypeptides have a complicated sequence of amino acids, particularly on one end, for capture and recovery of the desired material. The actual usefulness of the described materials is not demonstrated in the noted publication.

Such materials are believed to have a low expression yield. That is, often the level of expression is so low as to be detectable only using radioactive labeling of the cells, or antibodies specific to a particular tag or peptide sequence. The preparation of these materials is lengthy and tedious, requiring a costly purification procedure from cell paste lysates. Because of the low expression level, the production yield is also low. Because of the particular described capture mode, the removal of epitopic affinity tags by chemical or enzymatic means is tedious and costly with no certainty of complete removal. Thus, some of the molecules have extraneous amino acids that are not part of the desired collagen-like sequence.

It would be useful to have a way to prepare photographic emulsions using highly uniform and easily prepared collagen-type peptizers. It would be particularly useful to be able to control grain morphology with particular peptizers so that emulsions could be prepared having specific types of silver halide grains.

SUMMARY OF THE INVENTION

We have overcome the problems noted above with a method for preparing a thin tabular silver halide emulsion in which the halide content is at least 50 mole percent bromide, and wherein tabular grains of less than 0.30 µm in thickness and having an aspect ratio greater than 5 account for more than 50% of the total grain projected area, the method comprising:

nucleating silver halide grains in the presence of a nucleation peptizer, and thereafter growing the silver halide grains in the presence of a growth peptizer, wherein the nucleation or growth peptizer is a synthetic biopolymer having low binding affinity for silver ion.

This invention also provides a method for preparing a non-tabular silver halide emulsion, the method comprising:

nucleating silver halide grains in the presence of a nucleation peptizer, and thereafter growing the silver halide grains in the presence of a growth peptizer, wherein the nucleation or growth peptizer is a synthetic biopolymer having high binding affinity for silver ion.

Moreover, the present invention comprises a process for preparing a silver halide emulsion in a reaction mixture, the process comprising nucleating or growing silver halide grains in the reaction mixture in the presence of a biopolymer peptizer having at least one occurrence of the following peptide sequences identified herein as Formulae I, II and III, respectively:

$$\{[(Gly\ Pro\ Gln)(Gly\ Pro\ Glu)_4]_2\}_n \qquad I$$

$$Gly\ Pro\ Glu\{[(Gly\ Pro\ Gln)(Gly\ Pro\ Glu)_4]_2\}_n \qquad II$$

Gly Pro Xaa$_1$ Gly Leu Xaa$_2$ Gly Pro Arg Gly Pro Pro Gly Ala Ser Gly Ala Pro Gly Pro Glu Gly Phe Gln Gly  III wherein Xaa$_1$ and Xaa$_2$ are independently the amino acids identified as Met, Ile, His, Lys, Asn, Tyr or Gln, and n is 1 to 25.

This invention also provides a silver halide emulsion prepared by the process described above.

Moreover, it also provides a photographic element comprising a support having thereon at least one imagewise exposable layer, that layer comprising a silver halide emulsion prepared by the described process.

The present invention provides considerable advantages over the use of conventional peptizers. The synthetic polypeptides used herein are highly uniform in properties, are readily prepared in either small or large quantities, and can be readily modified by the choice of amino acids to provide silver halide emulsions having specific grain morphology. These peptizers can be used for either nucleation or growth of silver halide grains, and can readily be used alone or in combination with conventional binders in photographic emulsion vehicles.

The specific biopolymers described herein are representative of the biopolymers that can be used to prepare silver halide emulsions of specific morphology. Depending upon the specific amino acids included in the chain and their locations, the biopolymer peptizer can have either high affinity or low affinity for silver ion, and as such, can provide specific grain morphology associated with the specific affinity. Thus, we have found a way to control grain morphology with the use of biopolymer peptizers having specifically designed amino acid sequences.

DETAILED DESCRIPTION OF THE INVENTION

Figure 1A:
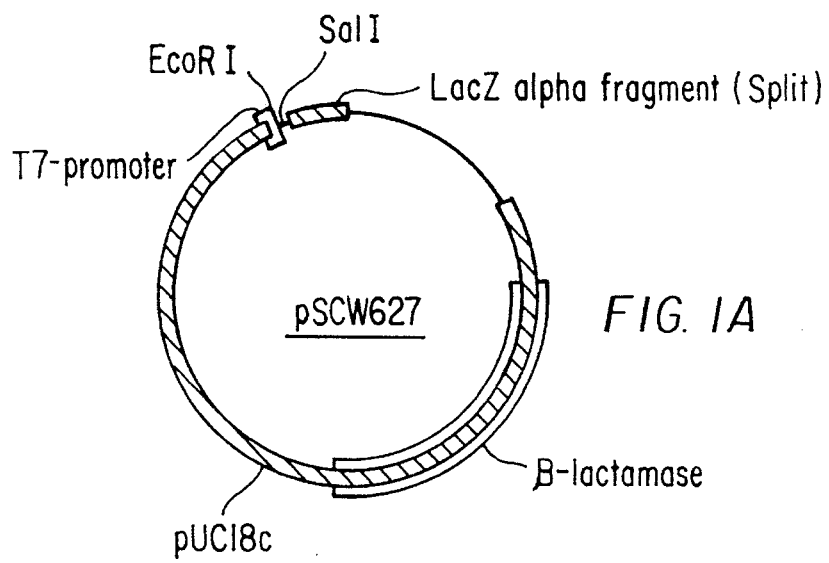
FIGS. 1A, 1B and 1C are schematic diagrams of cloning plasmids used in the recombinant preparation of one biopolymer useful in of the present invention, as described in Preparation 1 below.

In describing the present invention, the following definitions must be understood for this entire application:

As applied to silver halide grains, the term "thin" as used herein refers to an average grain thickness of less than 0.15 μm as measured in an electron micrograph.

"Aspect ratio" is defined as the ratio of the equivalent circular diameter to the average grain thickness. A "high aspect ratio" is one that is greater than about 6.

"Equivalent circular diameter" refers to the diameter of a circle having the same projected area as the projected area of the silver halide grain.

Non-tabular morphologies, include but are not limited to cubic, octahedral, rod-shaped and spherical morphologies, and tabular grains having an aspect ratio less than about 5.

Unless otherwise indicated, the term "about", when used to modify concentrations or dimensions, is meant to mean ±10% of the indicated value, when used to define pH and aspect ratio, refers to ±0.5 pH or aspect ratio value, and when used to define temperature, refers to ±5° C.

The term "polypeptide" is used herein to refer to sequences having at least 20 amino acids, such sequences having at least one occurrence of one or more of the peptide sequences identified herein as Formulae I, II and III, or a tripeptide contained in these three peptide sequences.

The terms "biopolymer" and "protein" are used interchangeably and are meant to refer to molecules having more amino acids than the specific polypeptides described herein, but including at least one of those polypeptides.

"Binding affinity for silver" refers to measure of the capacity of a given polypeptide or biopolymer to bind with silver ion. It is determined by measuring the differences in silver potential (Δ vAg) between that of a phosphate buffer solution (pH 7.0) of silver nitrate ($5 \times 10^{-6}$ molar), potassium nitrate (0.1 molar) and the polypeptide or biopolymer (0.3 weight %), compared to a similar solution without the polypeptide or biopolymer. Potential is measured using a bare silver electrode against a silver/silver chloride reference electrode in a salt bridge assembly.

"Low binding affinity" is defined as a Δ vAg of 50 mV or less. "High binding affinity" is defined as a Δ vAg of greater than 50 mV.

Amino acids are described herein by the conventional three letter symbols, and nucleotides are identified using the conventional single-letter symbols for individual bases.

The polypeptides, biopolymers or nucleic acids useful in the practice of this invention are not known to occur in nature in an isolated state.

The polypeptides particularly useful herein have one of the following peptide sequences identified herein as Formulae I, II and III, respectively:

$$\{[(Gly\ Pro\ Gln)(Gly\ Pro\ Glu)_4]_2\}_n \qquad I$$

$$Gly\ Pro\ Glu\{[(Gly\ Pro\ Gln)(Gly\ Pro\ Glu)_4]_2\}_n \qquad II$$

Gly Pro Xaa$_1$ Gly Leu Xaa$_2$ Gly Pro Arg Gly Pro Pro Gly Ala Ser Gly Ala Pro Gly Pro Glu Gly Phe Gln Gly  III wherein Xaa$_1$ and Xaa$_2$ are independently the amino acids identified as Met, Ile, His, Lys, Asn, Tyr or Gln, and n is 1 to 25.

In the foregoing Formulae I and II, it is preferred that n is from 3 to 20, and more preferred that n be from 3 to 18.

In one embodiment, Xaa$_1$ and Xaa$_2$ in Formula III are the same amino acids, such as Ile, Lys, Asn, Tyr or Gln. Most preferably, each of Xaa$_1$ and Xaa$_2$ is Gln. The polypeptides of this embodiment generally have a low binding affinity for silver ion, and thus are particularly useful for preparing thin tabular grains. Other biopolymers useful for preparing thin tabular grains include Formulae I and II wherein n is 3 to 18. As shown below in Examples 2 and 3, such biopolymers (SEQ ID NO:6–10) provide photographic emulsions having grains with thin tabular morphology.

In a second embodiment, useful biopolymers are represented by Formula III having Met or His for both of $Xaa_1$ and $Xaa_2$.

In a third embodiment, useful biopolymers are represented by Formula III wherein $Xaa_1$ is Ile and $Xaa_2$ is Met, or $Xaa_1$ is Met and $Xaa_2$ is Ile.

The polypeptides of the second and third embodiments generally have a high binding affinity for silver ion, and thus are particularly useful for preparing emulsions other than tabular silver bromide or silver bromoiodide emulsions (such as octahedral or irregular). As shown in Examples 1 and 3 below, such biopolymers (SEQ ID NO:11–14) provide silver bromide or silver bromoiodide photographic emulsions having non-tabular morphologies. It is contemplated, however, that biopolymers within the scope of this invention could be designed to have strong binding to silver ion and be useful in preparing silver chloride emulsions with desired morphologies.

Particularly useful peptide sequences found in the polypeptides and biopolymers useful in the practice of this invention include:

SEQ ID NO:1:

Gly Pro Glu {[(Gly Pro Gln)(Gly Pro Glu)$_4$]$_2$}$_3$

SEQ ID NO:2:

Gly Pro Glu {[(Gly Pro Gln)(Gly Pro Glu)$_4$]$_2$}$_4$

SEQ ID NO:3:

Gly Pro Glu {[(Gly Pro Gln)(Gly Pro Glu)$_4$]$_2$}$_9$

SEQ ID NO:4:

{[(Gly Pro Gln)(Gly Pro Glu)$_4$]$_2$}$_1$

SEQ ID NO:5:

{[(Gly Pro Gln)(Gly Pro Glu)$_4$]$_2$}$_{18}$

SEQ ID NO:6:

Gly Pro Ile Gly Leu Ile Gly Pro Arg Gly Pro Pro Gly Ala Ser Gly Ala Pro Gly Pro Glu Gly Phe Gln Gly

SEQ ID NO:7:

Gly Pro Lys Gly Leu Lys Gly Pro Arg Gly Pro Pro Gly Ala Ser Gly Ala Pro Gly Pro Glu Gly Phe Gln Gly

SEQ ID NO:8:

Gly Pro Asn Gly Leu Asn Gly Pro Arg Gly Pro Pro Gly Ala Ser Gly Ala Pro Gly Pro Glu Gly Phe Gln Gly

SEQ ID NO:9:

Gly Pro Tyr Gly Leu Tyr Gly Pro Arg Gly Pro Pro Gly Ala Ser Gly Ala Pro Gly Pro Glu Gly Phe Gln Gly

SEQ ID NO:10:

Gly Pro Gln Gly Leu Gln Gly Pro Arg Gly Pro Pro Gly Ala Ser Gly Ala Pro Gly Pro Glu Gly Phe Gln Gly

SEQ ID NO:11:

Gly Pro Met Gly Leu Met Gly Pro Arg Gly Pro Pro Gly Ala Ser Gly Ala Pro Gly Pro Glu Gly Phe Gln Gly

SEQ ID NO:12:

Gly Pro His Gly Leu His Gly Pro Arg Gly Pro Pro Gly Ala Ser Gly Ala Pro Gly Pro Glu Gly Phe Gln Gly

SEQ ID NO:13:

Gly Pro Ile Gly Leu Met Gly Pro Arg Gly Pro Pro Gly Ala Ser Gly Ala Pro Gly Pro Glu Gly Phe Gln Gly

SEQ ID NO:14:

Gly Pro Met Gly Leu Ile Gly Pro Arg Gly Pro Pro Gly Ala Ser Gly Ala Pro Gly Pro Glu Gly Phe Gln Gly

SEQ ID NO:15:

{[(Gly Pro Gln)(Gly Pro Glu)$_4$]$_2$}$_9$ and

SEQ ID NO: 16:

Gly Pro Glu {[(Gly Pro Gln)(Gly Pro Glu)$_4$]$_2$}18

A most preferred polypeptide has the peptide sequence identified above as SEQ ID NO:15 for making grains having tabular morphology. Other polypeptides could be preferred for making other types of grains.

The polypeptides described herein can be used as isolated peptide sequences, or they can be included as polypeptide sequences of biopolymers. Thus, the useful biopolymer peptizers can have one or more occurrences of one or more of the noted peptide sequences, or any combination thereof. More particularly, such biopolymers generally have multiple occurrences of the peptide sequences, for example, at least 3 and up to 25 occurrences. Moreover, the biopolymers can have one or more occurrences of a combination of two or more of the noted peptide sequences.

The biopolymers useful in the practice of the present invention can be prepared in a number of ways. For example, they can be prepared using conventional fMoc peptide synthesis, as described in *Synthetic Peptides: A User's Guide,* W.H. Freeman, Inc., 1992. Thus, the polypeptides can be prepared using these techniques, including purification to greater than 99.7% full length purity by reverse phase high performance liquid chromatography. The identity of the purified biopolymer can be confirmed by amino acid analysis. The usual amounts of biopolymers prepared in this manner is on the order of a few milligrams up to a few grams. Chemical synthesis of a biopolymer is described in more detail in the Preparatory Method 2 immediately preceding the examples.

The biopolymers can also be prepared using conventional DNA recombinant techniques (consider, for example, *Recombinant DNA*, 2nd Ed., W.H. Freeman, Inc., 1992, *Molecular Cloning: A Laboratory Manual*, 2nd Ed., Vols. I, II and III, Cold Spring Harbor Press, 1989, *Guide to Molecular Cloning Techniques, Methods in Enzymology*, Vol. 152, Academic Press, Inc., 1987, *Guide to Yeast Genetics and Molecular Biology, Methods in Enzymology*, Vol. 194, Academic Press, Inc., 1991 among many other well known textbooks and journal publications). Conventional protein expression procedures using various bacterial or yeast host cells can be practiced, as well as conventional purification techniques. The host cells typically containing a recombinant vector that comprises the nucleic acid of interest operationally linked to nucleic acid sequences that allow expression of the desired nucleic acid in the host cells.

Further, the biopolymers can be prepared using a novel preparatory procedure that involves the use of baker's yeast, *Saccharomyces cerevisiae*, as the host cell for polypeptide expression, in the presence or absence of an N-terminus eight amino acid epitope (identified as the FLAG™ epitope, owned by Immunex Corp. and described more fully by Hopp et al, *Biotechnology*, 6, 1204–1210, 1988) and several additional amino acids including a proteolytic trypsin site for cleavage removal at a particular lysine. Specific details of this preferred and novel preparatory method using recombinant DNA technology and a specific sequence of purification steps are presented in the Preparatory Method 1 immediately preceding the examples below.

In general, the method of the present invention for preparing photographic emulsions is carried out by concurrently adding silver and one or more halide ions into an appropriate emulsion reaction vessel that contains water as the dispersing medium. The silver ions are preferably supplied in an aqueous solution of silver nitrate, or other silver salt. The halide ions (such as chloride, bromide, iodide or mixtures thereof) are preferably supplied in one or more aqueous solutions of ammonium or alkali metal salts. The introduction of these solutions during emulsion precipitation is managed in a number of ways, some of which are described in U.S. Pat. No. 4,334,012 (Mignot) and U.S. Pat. No. 4,713,320 (Maskasky), incorporated herein by reference for that technology. In the preparation of thin tabular grains, introduction of silver and halide ions in the form of Lippmann emulsions is also contemplated.

The silver halide grains prepared in the practice of this invention can include grains composed of silver bromide, silver chloride, silver chlorobromide, silver bromoiodide, silver iodobromochloride or other photographically useful silver halides that provide face centered grain lattice structures.

Mixtures of the biopolymers can be used as nucleation or growth peptizers in making emulsions, if desired. In addition, one or more biopolymers can be used in a mixture with one or more conventional nucleation or growth peptizers or binders, or they can be added separately from such materials. While it is possible to add conventional peptizers as a co-peptizer toward the end of precipitation, it is preferred to use the biopolymer as the sole peptizer throughout nucleation and growth of the silver halide grains. Such co-peptizers may include oxidized gelatin as well as any other suitable hydrophilic polymer or protein known for this purpose.

In addition to serving as peptizers, the biopolymers may be useful as growth modifiers in emulsion preparation, as described for example in U.S. Pat. No. 5,178,997 (Maskasky) and U.S. Pat. No. 5,178,998 (Maskasky).

As is known in the art, the reaction mixture can additionally contain various other additives commonly used in emulsions, either initially in the reaction vessel, or added separately or in combination with any other component. Such compounds include, but are not limited to, modifying compounds (such as copper, thallium, lead, bismuth, cadmium, zinc, middle chalcogens, gold and Group VIII noble metals), which can be in the form of labile complexes or incorporated non-labile complexes. Additionally, chemical sensitizers, spectral sensitizing dyes, color-forming couplers, antifoggants, stabilizers, image forming modifying compounds and coating aids may be included in the reaction mixture as would be understood by one skilled in the art.

Conventional binders can also be included in the emulsions. Such materials include, but are not limited to, gelatin, gelatin-derivatives, hydrophilic synthetic polymers and other materials known in the art. Gelatin is a preferred binder.

In preferred embodiments of this invention, thin tabular grains (sometimes known as "T-GRAINS") are formed in photographic emulsions using biopolymer peptizers that have a low affinity for silver ions. Such emulsions are prepared using procedures well known in the art, including the Maskasky patent noted above, which is incorporated herein by reference for such technology. Such emulsions are generally composed of silver halide grains having at least 50% mole percent of bromide (such as silver bromide or silver iodobromide grains), a thickness less than about 0.30 μm and an aspect ratio of at least 5. Preferably, the grains have a thickness less than about 0.20 μm (more preferably, less than about 0.07 μm) and an aspect ratio from about 6 to about 100. Preferably, such grains account for at least 70%, more preferably at least 90%, and most preferably at least 97% (molar) of the total grain projected area in the emulsion. Additional details of thin tabular grain emulsions are provided, for example, in U.S. Pat. No. 5,176,991 (Jones et al), U.S. Pat. No. 5,176,992 (Maskasky et al), U.S. Pat. No. 5,178,997 (Maskasky), U.S. Pat. No. 5,178,998 (Maskasky et al), U.S. Pat. No. 5,183,732 (Maskasky), U.S. Pat. No. 5,185,239 (Maskasky) and EP-A-0 534 395 [published Mar. 31, 1993, relating to (100) tabular silver chloride emulsions], all of which are incorporated herein by reference.

The emulsions prepared by the present invention can be negative-working or positive-working and can be incorporated into a photographic element as precipitated in any suitable manner. However, preferably they are further adapted to serve specific photographic uses by procedures that are well known in the art. The various emulsions can be blended with conventional emulsions formed without the biopolymer peptizers described herein, mixed with various vehicles or hardeners, washed, or chemically and spectrally sensitized (such as taught in U.S. Pat. No. 4,439,520 of Kofron et al). Various known separation procedures can also be applied if desired. It is contemplated that the present invention can include any and all aspects of the conventionally known emulsions useful in the photographic art, including those materials described in *Research Disclosure*, publication 36544, pages 501–541 (September, 1994). *Research Disclosure* is a publication of Kenneth Mason Publications Ltd., Dudley House, 12 North Street, Emsworth, Hampshire PO10 7DQ England (also available from Emsworth Design Inc., 121 West 19th Street, New York, N.Y. 10011). This reference will be referred to hereinafter as "*Research Disclosure*".

The present invention also provides photographic elements comprising one or more emulsions of the present invention disposed as imagewise exposable layers, or as segments of one or more layers, on a suitable support. Such elements can include only emulsions of the present invention, or only a single such emulsion in combination with one or more conventional emulsions. Such elements can include black-and-white and color (single or multilayer) elements to serve various applications, including but not limited to, photographic films and papers, image transfer materials, photothermography, and radiography. They can include one or more other layers such as filter layers, overcoats, interlayers, subbing layers and other layers well known in the art. The element may also contain a magnetic backing. The noted "*Research Disclosure*" provides more details of such elements, and how the present emulsions could be adapted thereto would be readily apparent to one skilled in the art.

The photographic elements of this invention can be exposed to radiation to form a latent image and processed to form a developed image using known processes and equipment. Further processing of developed images would be readily accomplished using known processing methods and solutions, as described for example, in "*Research Disclosure*," noted above.

Preparatory Method 1 for Making Biopolymer Using DNA Recombinant Technology:

This preparation demonstrates a preferred method for preparing a biopolymer useful in the practice of this invention. Specifically, it illustrates the use of *Saccharomyces cerevisiae* (*S. cerevisiae*) as the host organism to prepare the polypeptide (or biopolymer) identified herein as SEQ ID NO:3. This biopolymer comprises the amino acid sequence "Gly-Pro-Glu" followed by 9 replicates of the polypeptide sequence SEQ ID NO:4, also identified herein as the "GG monomer".

To prepare a double strand nucleic acid that encodes the GG monomer, a sequence with optimum codon usage for *S. cerevisiae* was chosen. Two complementary DNA oligonucleotides encoding the GG monomer were chemically synthesized by standard automated trityl phosphoamidate reactions (F. Eckstein, *Oligonucleotide and Analogs*, Oxford University Press, Oxford, England, 1991). The top strand was the encoding strand. Additional sequences needed for cloning of the hybridized oligonucleotides and the directional assembly of the DNA fragments into DNA concatenated polymers that code for biopolymers are also included in these oligonucleotides (as described below).

The top strand oligonucleotide had the sequence:

5'-AATTCGGTCC CGAGGGTCCA CAAGGTCCAG AAGGTCCAGA
AGGTCCAGAA GGTCCAGAAG GTCCACAAGG TCCAGAAGGT CCAGAAGGTC
CAGAAGGTCC CGAGCTAAG-3'

SEQ ID NO:17

The complementary bottom strand oligonucleotide had the sequence:

5'-TCGACTTAGC TCGGGACCTT CTGGACCTTC TGGACCTTCT
GGACCTTGTG GACCTTCTGG ACCTTCTGGA CCTTCTGGAC CTTCTGGACC
TTGTGGACCC TCGGGACCG-3'

SEQ ID NO:18

Inside the ends of these two oligonucleotides were encoded Ava I nonpalindromic restriction sites (underlined in SEQ ID NO:17) which, upon proper manipulation, oriented the directional assembly of DNA fragments into repeated head-to-tail DNA concatamers, encoding repeated biopolymers. For SEQ ID NO:3 biopolymer, the form of the Ava I site chosen was:

| top strand: | CCCGAG |
| bottom strand: | GGGCTC |

This Ava I sequentially encoded a pro-glu dipeptide which is part of the desired polypeptide sequence. Upon assembly of this fragment into an array of repeated DNA fragments, the result was a perfect coding for the biopolymer with no amino acids other than those in the noted GG monomer sequence.

The two oligonucleotides, upon hybridization, formed a double stranded nucleic acid having cohesive ("sticky") ends for the restriction sites Eco RI and Sal I. Hybridization was carried out in a solution of tris(hydroxymethyl)aminomethane buffer (10 mmolar, pH 8), containing ethylenediaminetetraacetic acid (1 mmolar) and the oligonucleotides (20 μg/ml of each). Hybridization was begun at 95° C., and the reaction mixture was gradually cooled to 25° C. at a rate of 1° C./15 minutes. Hybridization was determined to be successful by analysis for the presence of a single narrow band of the correct double strand molecular weight upon electrophoresis in a conventional 6% polyacrylamide gel [using tris(hydroxymethyl)aminomethane, borate and ethylenediaminetetraacetic acid], or by a cooperative thermal denaturation observed by a hyperchromic increase in absorbance at 260 nm.

Figure 1B:
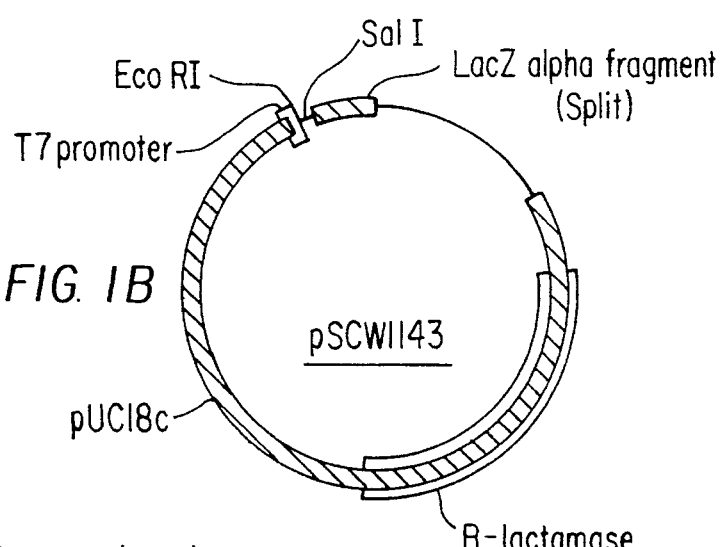
Figure 1C:
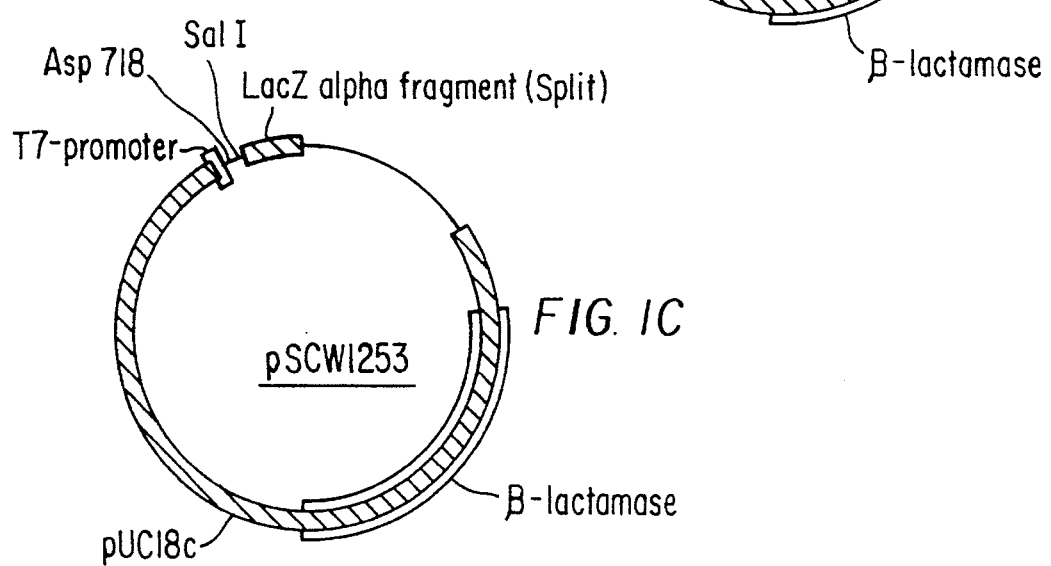

This hybridized fragment was then ligated into the Eco RI and Sal I sites of a modified derivative of the commercially available pTZ18R Genescribe plasmid that has a shortened polylinker consisting of Eco RI, Ava I, Sal I, Hind III (pSCW627), as shown in FIG. 1. This and other modified pTZ18R Genescribe derivatives are biopolymer cloning vectors, because this is where monomer DNA or repeated multimers are cloned after oligonucleotide hybridization (cloning of what is identified as "GG monomer DNA") or directional assembly (cloning of "multimer GG" DNA). Three such cloning vectors are pSCW627, pSCW1143, pSCW1253, as shown in FIGS. 1A–1C. The plasmid pSCW627 was used for cloning the Eco RI-Sal I hybridized oligonucleotide pair, whereas pSCW1143 was used for the cloning of repeated GG monomer DNA to produce DNA encoding for the amino acid sequence Glu Phe Gly Lys Gly Pro Glu{[(Gly Pro Gln)(Gly Pro Glu)$_4$]$_2$}$_n$ wherein the underlined Lys is the lysine that ultimately will be cleaved in the biopolymer by Trypsin to remove the N-terminal FLAG™ epitope [the Asp Tyr Lys (Asp)$_4$ Lys FLAG™ epitope sequence is encoded by the yeast expression plasmid]. The N-terminal FLAG™ epitope generally provides for analytical detection by conventional anti-FLAG® monoclonal antibodies, M$_1$ or M$_2$, to the [Asp Tyr Lys (Asp)$_4$ Lys] FLAG™ epitope sequence in conjunction with the use of conventional Western blots.

Plasmid pSCW1253 was used for the "landing" (or cloning) of repeated GG monomer DNA that ultimately was used to secrete the biopolymer sequence Formula II devoid of the presence of any nonpolymer amino acids as used in pSCW1143 constructions (that is, the N-terminal FLAG™ epitope from the yeast expression plasmid, the amino acids encoded by the restriction enzyme site, Eco RI, and the Gly-Lys dipeptide for Trypsin cleavage).

The assembly of repetitive DNA monomers was separated into repeating multimers, and the potential recombination toxicity of direct repeats of DNA was separated from the actual production of the secreted amino acid biopolymer and the potential protein toxicity to the cell by using two different organisms (a prokaryote and an eukaryote). First, the repetitive DNA was initially cloned in *E. coli* with the reading frame of the inserts out of the reading frame of lacZ match the desired encoded monomer sequence as determined by fluorescent DNA sequencing on a conventional Applied Biosystems 390 instrument using standard procedures.

The sequenced GG monomer DNA, inserted into pSCW627 and identified as pSCW1109 DNA is shown as follows in Schematic 1:

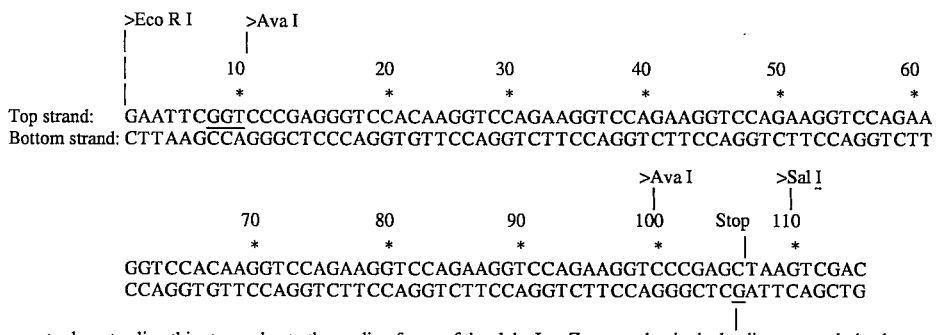

extra base to align this stop codon to the reading frame of the alpha Lac Z start codon in the landing vector derived from pTZ18R Genescribe so that there is a good blue to white screen for the presence of cloned inserts in the vectors pSCW627, pSCW1143 and pSCW1253. Second, the biopolymer was produced by secretion in the baker's yeast, *S. cerevisiae*.

A mixture of the hybridized GG monomer DNA as described above was ligated into the Eco RI and Sal I sites of pSCW627 with T4 DNA ligase at 16° C. for 16 hours by standard methods. The ligation reaction was then transformed into *E. coli* strain JM109 [genotype e14⁻(mcrA), recA1, endA1, gyrA96, thi-1, hsdR17($r_k-$, $m_{k+}$), supE44, relA1, Δ(lac-proAB), (F' traD36, proAB, lacI$^q$ZΔf15)] that had been made competent by a standard calcium chloride procedure and stored at −80° C. (see *Molecular Cloning: A Laboratory Manual*, noted above). The transformation reaction was plated onto X-GAL (80 μg/ml) LB plus ampicillin (150 μg/ml) plates and incubated at 37° C. Transformants were picked into liquid LB plus ampicillin media, grown overnight at 37° C., and plasmid DNA prepared by standard methods.

The presence of clones containing inserts was analyzed by Eco RI-Sal I double digests and by Ava I solo digests. Clones containing the hybridized oligonucleotide insert were white, because the oligonucleotide Eco RI-Sal I fragment has an in-frame stop codon included between the last Ava I site and the Sal I site, which ensures a convenient X-GAL blue/white color transformation assay for the presence of the hybridized GG monomer.

A monomer fragment called "AG monomer", in which the encoded glutamines had been replaced by encoded asparagines, was also cloned in parallel.

Figure 2A:
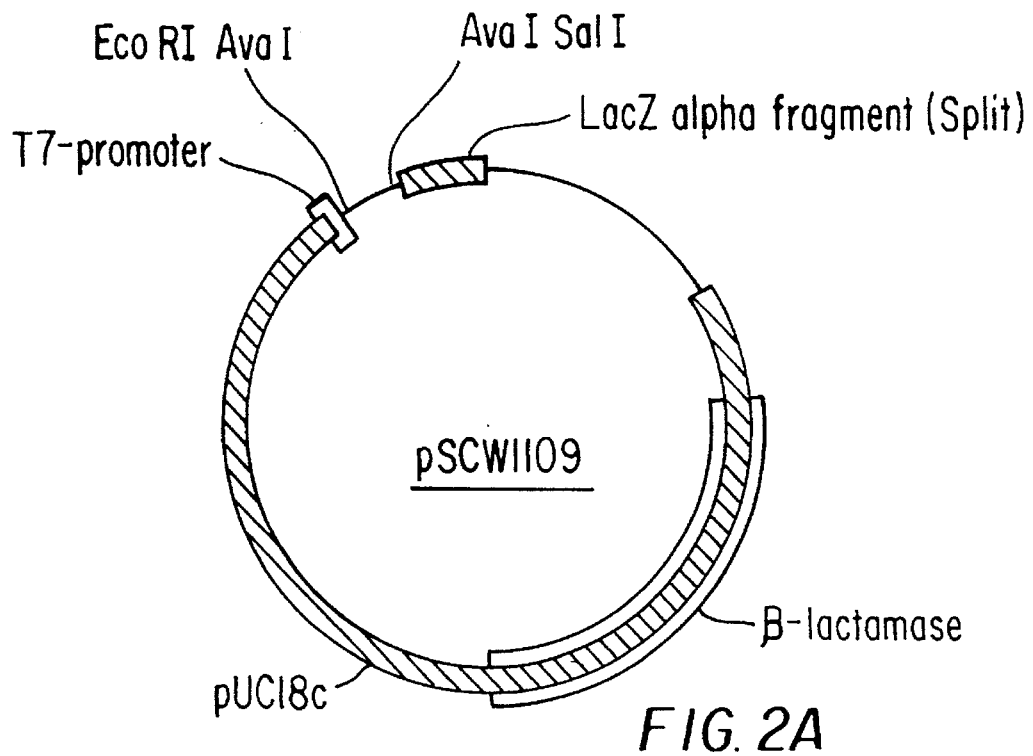
FIGS. 2A and 2B are schematic diagrams of certain "monomer plasmids" used in the recombinant preparation of one biopolymer useful in the practice of the present invention, as described in Preparation 1 below.
Figure 2B:
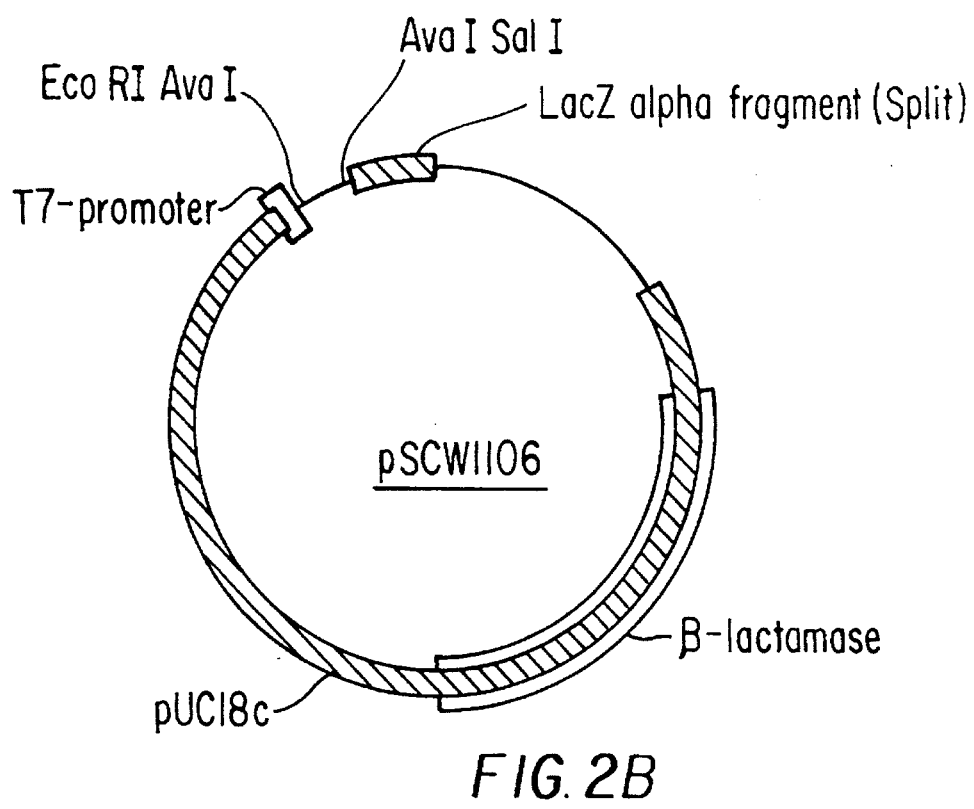

Two plasmids, pSCW1109 and pSCW1106 (see FIG. 2) were found to have putative monomer inserts of GG monomer and AG monomer, respectively, of the correct size, as determined using gel electrophoresis and conventional molecular weight markers. No evidence of plasmid instability due to recombination of the GG monomer or AG monomer inserts was observed.

The GG and AG monomers encoded in the two plasmids, pSCW1109 and pSCW1106, respectively, were found to A sample (1 mg) of pSCW1109 DNA was prepared by the method of Lee et al from a culture grown in the noted medium including ampicillin (150 μg/ml). The Ava I monomer nucleic acid encoding the GG monomer was prepared by restricting the pSCW1109 DNA with 2 Units of Ava I per μg DNA at 37° C. for 8 hours. A complete digest was obtained as determined from the presence of two bands at 90 bp and 2.9 kbp on a conventional agarose gel. The Ava I monomer DNA was separated from the plasmid backbone by preparative 2% w/v agarose electrophoresis using a buffered solution containing tris(hydroxymethyl)aminomethane, phosphate and ethylenediaminetetraacetic acid, and visualized by ethidium bromoiodide staining and fluorescence. The agarose strip containing the Ava I monomer DNA was cut out of the gel and purified by a glass milk procedure using US BIOCLEAN™ glass beads (available from US Biochemicals, Inc.) according to the instructions provided.

Multimers of the GG monomer (identified herein as "GG multimers") were prepared by self legating the GG monomer DNA with T4 DNA ligase under standard conditions at 16° C. until a distribution of polymer repeats from 2 to greater than 40 occurred, as determined by 0.7% w/v agarose electrophoresis. Size fractionated GG multimers were prepared: first, by separation on a preparative 0.7% agarose electrophoresis gel, secondly, by visualizing the bands by ethidium bromide staining and fluorescence, and thirdly, by cutting the multimer ladder distribution into agarose slices, each containing a given size pool of repeats of GG monomer, (3 to 6, 7 to 11, 12 to 17, 18 to 24, 25 to 33 and lastly to the top of the multimer distribution). Finally, each multimer DNA pool was purified from the agarose gel slice by the glass milk procedure (noted above).

Each size fractionated GG multimer pool was ligated by standard procedures at 16° C. overnight with T4 DNA ligase into pSCW1143 or pSCW1253 at the Ava I site (FIGS. 1A–1C) which had been dephosphorylated by standard procedures with calf intestinal phosphatase or shrimp alkaline phosphatase. Dephosphorylation insures a greater percentage of insert containing transformants when a single restriction site is used for cloning.

Figure 3:
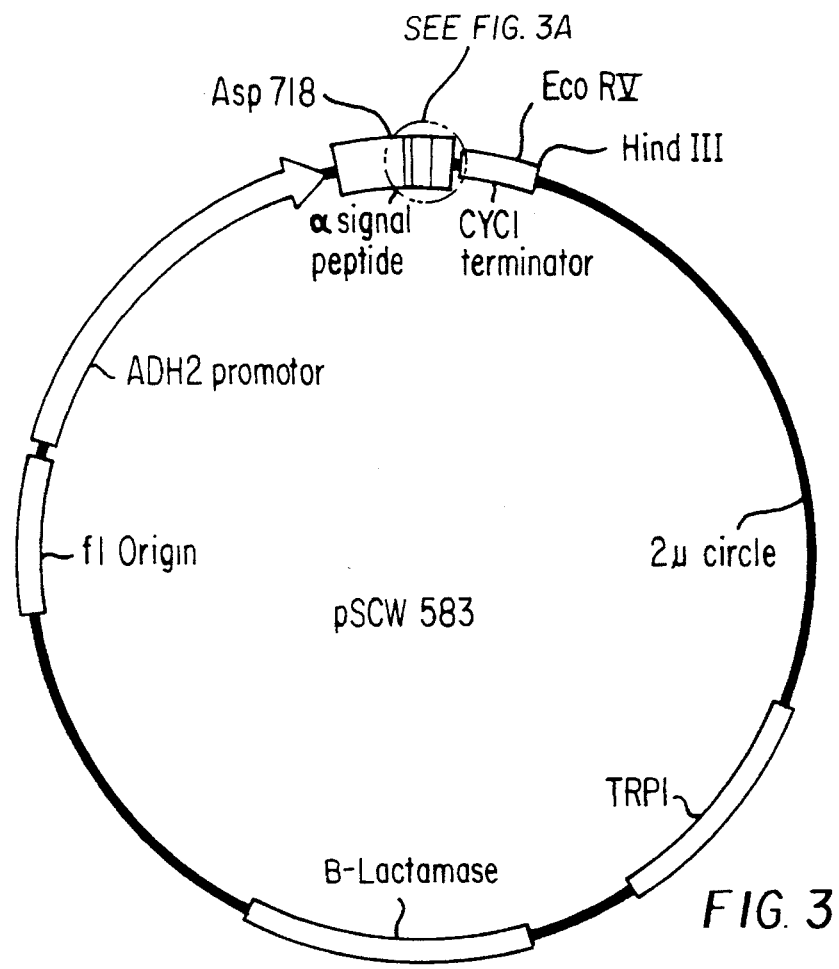
FIG. 3 is a schematic diagram of the baker's yeast expression plasmid used in the recombinant preparation of one biopolymer useful in the practice of the present invention, as described in Preparation 1 below.
Figure 3A:
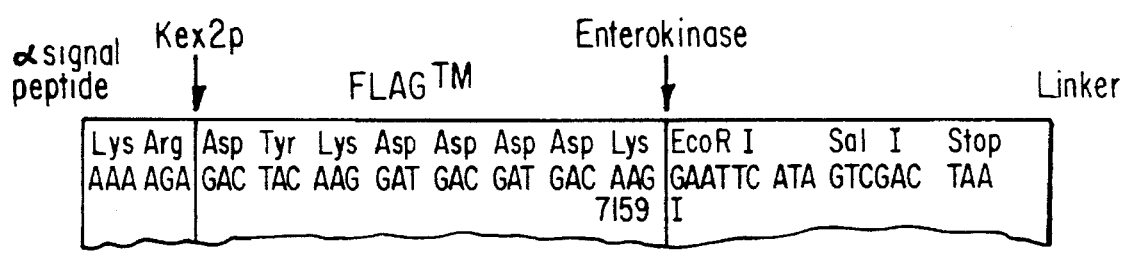
FIG. 3A is a cut-away portion of the plasmid shown in FIG. 3.

To produce the GG biopolymer having a FLAG™ epitope that is removable by Trypsin, the landing plasmid pSCW1143 is used. The plasmid encodes a lysine Trypsin cleavage site. Schematic 2 below (pSCW1143 linker) shows the reading frame that results from cloning of Eco RI-Sal I fragments containing Ava I multimers into the pSCW583 vector (FIG. 3), and not that in the lacZ reading frame of pSCW1143 (FIGS. 1A–1C). This illustrates the distinction of biopolymer DNA construction in *E. coli* from biopolymer secreted expression in *S. cerevisiae*. This Ava I site CCC GAG sequence, at which repeated GG monomer is inserted, is preceded first by a glycine codon to produce a starting GPE tripeptide in the GG biopolymer and secondly by a lysine codon acid for cleavage by the Trypsin protease. The Ava I site that precedes the stop codon and thus the biopolymer, as constructed, ends in a Gly-Pro-Glu tripepride.

Asp 718-Sal I fragment containing Ava I multimer fragments into pSCW583 (FIG. 3), and not that in the lacZ reading frame of pSCW1253 (FIGS. 1A–1C). This again illustrates the distinction of biopolymer DNA construction in *E. coli* from biopolymer secreted expression in *S. cerevisiae*. The Ava I site, CCC GAC sequence, at which repeated GG monomer is inserted, follows first a glycine codon to produce a starting Gly-Pro-Glu tripeptide in the GG biopolymer and secondly a lys-arg codon pair as a Kex2p protease cleavage site. Additionally, a glutamic acid codon precedes the stop codons as part of the Ava I site, such that the biopolymer ends in a Gly-Pro-Glu tripeptide.

Schematic 2 pSCW1143

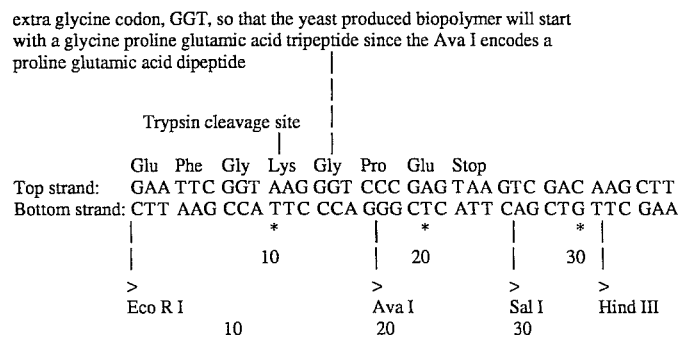

To produce the GG biopolymer without any extraneous amino acids, the landing plasmid pSCW1253 was used. The pSCW1253 plasmid encodes the C-terminus of the yeast Schematic 3 pSCW1253

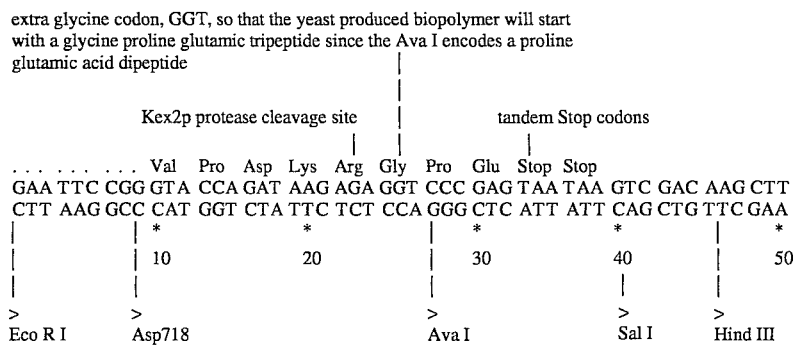

alpha factor secretory leader peptide, from the Asp 718 site to the encoded Lys Arg Kex2p protease site. The Kex2p protease cleaves the alpha secretion factor on the C-terminus side of the Lys Arg pair. Schematic 3 below (pSCW1253) also shows the reading frame that results from cloning of An Asp 718 site occurs in the yeast alpha factor signal secretion DNA sequence. The cleavage site for the yeast alpha signal protease, Kex2p (KEX2 gene product), is encoded in the yeast alpha factor signal DNA following this Asp 718 site. Therefore, a linker with an Asp 718 Sal I DNA fragment that encodes the amino acids normally found in the alpha factor secretion signal peptide from the Asp 718 up to the Kex2p cleavage site followed by the extra glycine codon and the appropriate Ava I site for landing GG multimers, was engineered. Biopolymer GG repeats were "landed" in this Ava I site, isolated and recloned into pSCW583 as Asp 718-Sal I DNA fragments. The result was GG multimer DNA that encodes and produces SEQ ID NO:22 GG biopolymers upon secretion from yeast.

Each GG multimer pool ligation, whether landed in the Ava I of pSCW1143 or pSCW1253, was transformed into *E. coli* strain JM109 as previously described. The presence of clones containing inserts in pSCW1143 were analyzed for multimer size by Eco RI-Sal I double digests compared to molecular weight standards whereas clones containing inserts in pSCW1253 were analyzed for multimer size by Asp 718-Sal I double digests. Multimer insert containing clones were checked by Ava I solo digests for verification of correct multimer assembly and absence of recombination artifacts. Typically, greater than 80% of the colonies on the transformation plate contained clonal multimers. These clones were all observed to be uniformly stable with the complete absence of recombination artifacts. Additionally, all GG monomer or multimer clones (in pSCW1143 and pSCW1253 backbones) were a brilliant sapphire blue color that was more intense than the blue of the non-insert containing plasmids (pSCW1143 and pSCW1253) in JM109 on LB X-Gal transformation plates.

Figure 4A:
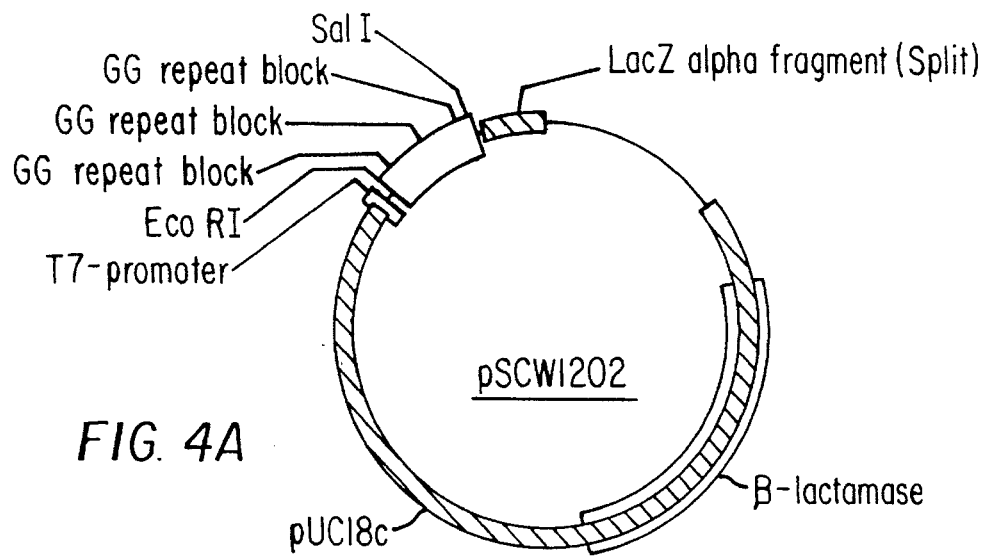
FIGS. 4A, 4B and 4C are schematic diagrams of the multimer plasmids used in the recombinant preparation of one biopolymer useful in the practice of the present invention, as described in Preparation 1 below.
Figure 4B:
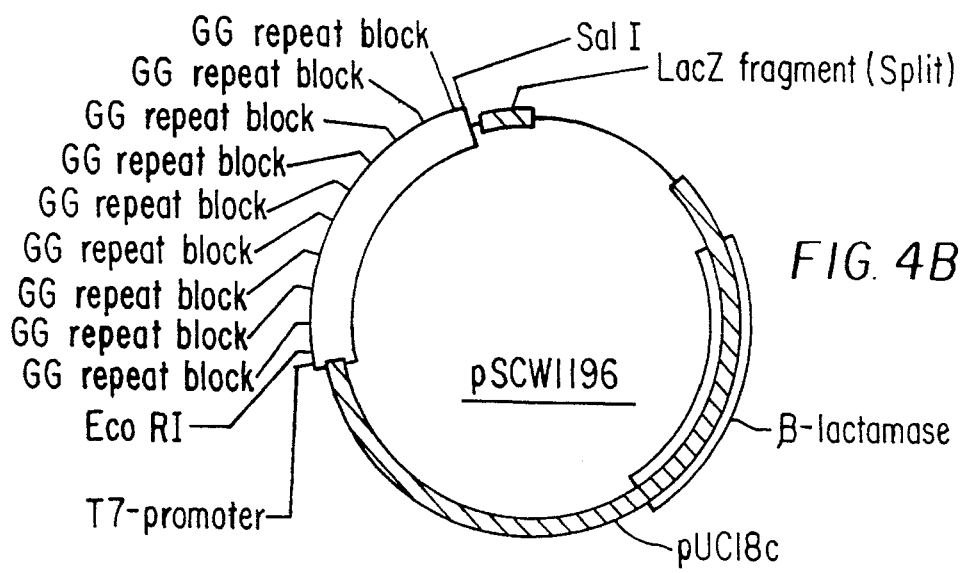
Figure 4C:
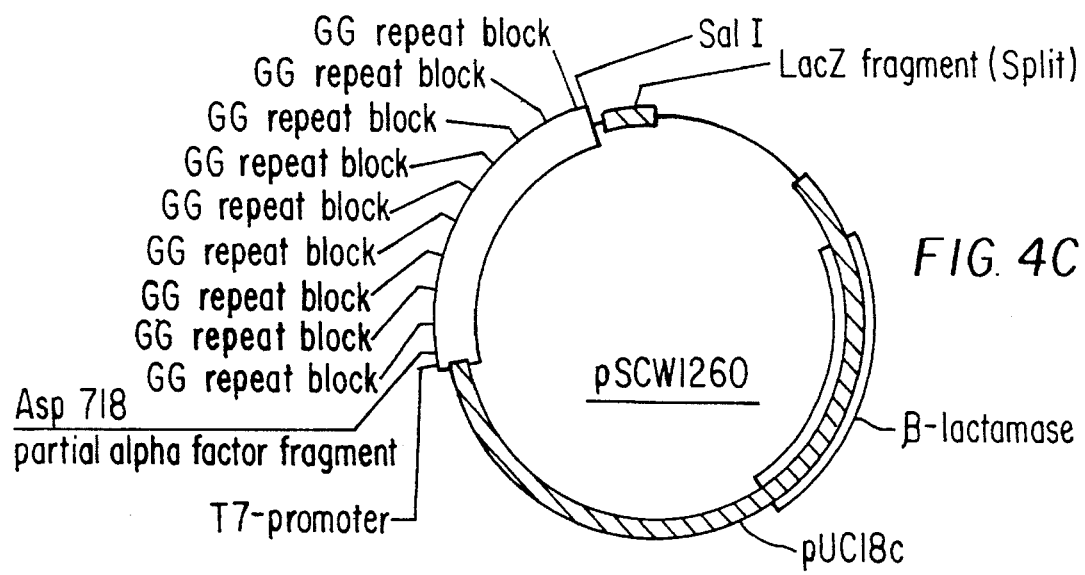

Two transformants in pSCW1143 backbones found to have the GG monomer DNA assembled into multimers of 3 and 9 were designated pSCW1202 and pSCW1196, respectively (FIGS. 4A and 4B). One transformant in a pSCW1253 backbone found to have the GG monomer DNA assembled into a multimer of 9 was designated pSCW1260 (FIG. 4C).

The baker's yeast protein expression vector pSCW583 contained DNA encoding the yeast alcohol dehydrogenase II promoter for regulated high transcriptional mRNA expression, the alpha factor pre-pro-region for translational initiation and extracellular secretion, the Kex2p cleavage site to remove the alpha factor pre-pro-region from the biopolymer, the FLAG™ epitope, a short Eco RI-Sal I polylinker to clone the assembled biopolymer, a CYC1 bidirectional transcriptional mRNA terminator, the yeast TRP1 gene for selection in yeast, yeast 2 micron circle elements for high copy plasmid control in yeast, the *E. coli* bla gene for antibiotic selection in *E. coli*, and pBR322 elements for high copy control in *E. coli*.

Multimers pSCW1202 (3 repeats of the GG monomer) and pSCW1196 (9 repeats of the GG monomer) were used as the source of a Eco RI-Sal I DNA polymer block containing the repeated GG monomer DNA for ligation at the same sites into the *S. cerevisiae* protein expression vector, PSCW583. Ligation of these DNA fragments was by the previously described standard method. The ligation reactions were transformed into *E. coli* strain JM109 and the transformants selected for ampicillin resistance by the previously described standard methods.

pSCW1260 (9 repeats of the GG monomer) was used as the source of Asp 718-Sal I DNA polymer block containing the repeated GG monomer DNA for ligation at the same sites into the *S. cerevisiae* protein expression vector, pSCW583. Ligation of these DNA fragments was carried out by the previously described standard method. The ligation reactions were transformed into *E. coli* strain JM109 and the transformants selected for ampicillin resistance by the standard methods previously described.

Figure 5A:
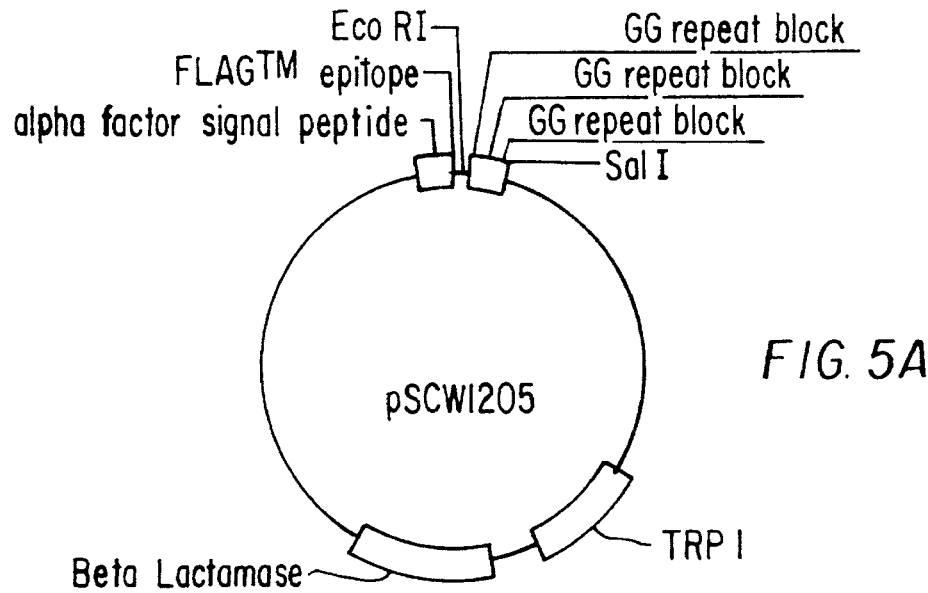
FIGS. 5A, 5B and 5C are schematic diagrams of the biopolymer yeast expression plasmids constructed and used in Preparation 1 below.
Figure 5B:
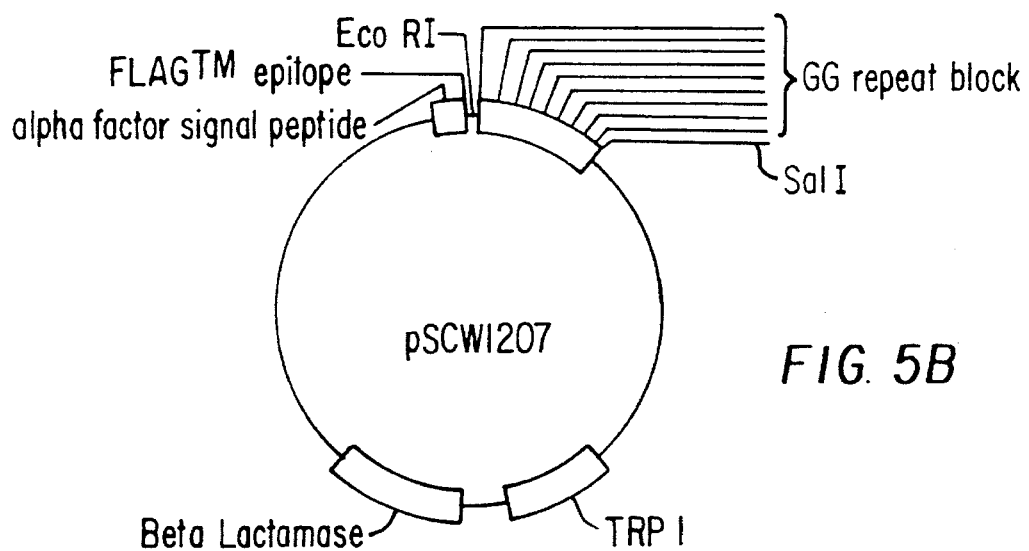

Transformants derived from the ligations of pSCW1202 and pSCW1196 multimer DNA (destined to be FLAG™ lysine epitope biopolymers) into the pSCW583 yeast expression vector were screened by Eco RI-Sal I double digests to confirm correct multimer size and by Ava I solo digests to confirm genetic stability. Two transformants were designated GG biopolymer yeast expression plasmids, pSCW1205 and pSCW1207 (FIGS. 5A and 5B). In yeast, pSCW1205 produces FLAG™ epitope Trypsin site N-terminally tagged 3 repeat GG biopolymer having the sequence:
SEQ ID NO: 19:

Asp Tyr Lys (Asp)$_4$ Lys Glu Phe Gly Lys* Gly Pro Glu {[(Gly Pro Gln)(Gly Pro Glu)$_4$]$_2$}$_3$, while pSCW1207 produces the sequence:
SEQ ID NO: 20:

Asp Tyr Lys (Asp)$_4$ Lys Glu Phe Gly Lys* Gly Pro Glu {[(Gly Pro Gln)(Gly Pro Glu)$_4$]$_2$}$_9$.

In this example, after production and purification, the extra N-terminus amino acids of the biopolymer were removed by Trypsin digestion at the lysine*. The bipolymer was re-purified and processed to the form of SEQ ID NO:3.

Figure 5C:
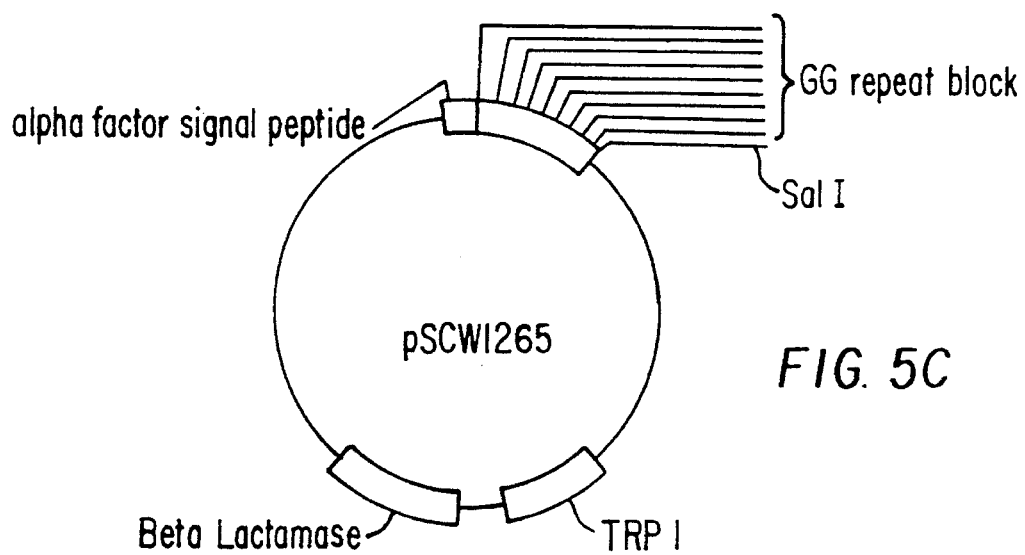

Transformants derived from the ligation of pSCW1260 multimer DNA (destined to be SEQ ID NO:3) into the yeast expression vector pSCW583 were screened by Asp718-Sal I double digests to confirm correct multimer size and by Ava I solo digests to confirm genetic stability. One transformant was designated pSCW1265 (FIG. 5C), that produces SEQ ID NO:3 in yeast.

pSCW1205 (SEQ ID NO:19), pSCW1207 (SEQ ID NO:20) and pSCW1265 (SEQ ID NO:3) were transformed by standard electroporation with a conventional Bethesda Research Electroporator into *S. cerevisiae* strain BJ3505 (available from the Yeast Genetic Stock Center, University of California, Berkeley). This strain has the genotype (mating type a pep4::HIS3 prbl-1.6R HIS3 lys2-208 trpl-101 ura3-52 gal2 can1). The protease deficient properties of this strain are well known. The pep4::HIS3 mutation inactivates the structural gene, PEP4, that encodes the PrA protease (an aspartic class endoprotease) whereas the prbl-1.6R mutation inactivates the structural gene, PRB1, that encodes the PrB protease (a serine class subtilisin-like endoprotease). Both PrA and PrB are lumenal vacuoler proteases. PrB in particular is expressed at high levels in stationary culture conditions.

Transformants were selected for TRP1 complementation on Synthetic Complete media (minus tryptophan) plates by standard methods (*Methods in Yeast Genetics, Laboratory Manual*, Cold Spring Harbor Press, 1981 and *Guide to Yeast Genetics and Molecular Biology, Methods in Enzymology*, Vol. 194, Academic Press, Inc., 1991).

BJ3505 transformants of pSCW1205, pSCW1207 and pSCW1265 were first grown for 48 hours on a roller at 30° C. to early stationary phase in 5 ml of liquid Synthetic Complete (minus tryptophan) media. These cultures were then rediluted to 1% v/v in 50 ml of the same media and grown on a rotary shaker at 175 revolutions per minute to early stationary phase (about 8 OD units at 600 nm) at 30° C. Finally, the culture were diluted to 4% by volume into one liter of production media and grown for 70 hours on a rotary shaker at 175 revolutions per minute at 30° C. in a 2.8 liter baffled fernbach flask. Several different production media may be used with or without the addition of calcium as a counter ion for the biopolymer and/or the yeast cell wall. YP1 production media contained 10% w/v yeast extract, 20% w/v Bactopeptone, 1% w/v dextrose and 3% w/v glycerol. YP4 production media contained 10% w/v yeast extract, 80% w/v Bactopeptone, 1% w/v dextrose and 3% w/v glycerol. Either a YP1 or YP4 optimized media supplemented with calcium chloride (20 millimolar) can be used for high production of GG biopolymers. YP1 production media supplemented with 20 mmolar calcium chloride provided a preferable compromise of high expression (about 500 mg/l) and low background of media protein impurities.

A pseudo plasticity in the GG biopolymer production culture was observed in some cases at 24 hours of culture growth when carefully examined and compared to a negative control culture. This pseudo plasticity rheologically shear thins when the culture was stirred with a rod. The pseudo plasticity occurs in a time dependent culture growth state only upon high level secreted expression of the SEQ ID NOS:1, 2, 3, 19 and 20 biopolymers (with or without the FLAG™ N-terminus epitope) and not for other secreted proteins. This phenomenon was observed much more easily in partially or purified GG biopolymer fractions. It is biopolymer length, concentration, temperature and ionic strength dependent, and lowers the specific gravity of the production culture broth compared to a negative control culture.

The purification of SEQ ID NO:20 (pSCW1207 in *S. cerevisiae* strain BJ3505) and the removal of the FLAG™ epitope to produce SEQ ID NO:3 is described below. Twenty liters of broth from BJ3505 transformed with pSCW1207 was prepared from twenty separate one liter fernbach cultures grown by the YP1 culture conditions described above. To remove the yeast cells and produce a culture supernatant (S1), the 20 liters of culture broth were centrifuged at 10,000 g for 10 minutes. The supernatant was sometimes filter sterilized using a 1,000,000 molecular weight cutoff conventional Filtron tangential flow filtration unit to produce a second supernatant (S2), that was devoid of yeast cells.

Twenty liters of either S1 or S2 were brought to pH 3.2 with hydrochloric acid to precipitate (overnight at 4° C.) the biopolymer preferentially over the other broth components. The acidified supernatants of S1 or S2 were centrifuged at 10,000 g for 20 minutes to produce a supernatant (S3) that was discarded, and a pellet (P3) containing the desired biopolymer. The P3 pellet was then resuspended in 2 liters (one tenth the original culture volume) of tris(hydroxymethyl)amino methane buffer (50 mmolar, pH 7.8) containing sodium chloride (200 mmolar), ethylenediaminetetraacetic acid (20 mmolar) and phenylmethylsulfonyl fluoride (1 mmolar) and clarified by centrifugation at 10,000 g for 20 minutes. The desired biopolymer (SEQ ID NO:20) was in the supernatant (S4), and the residual pellet (P4) was discarded.

The biopolymer was purified by ion exchange chromatography. The S4 supernatant was applied to a commercial 10 cm×30 cm (4 liter) DEAE Sephacel ion exchange column. The column was washed with 80 liters (20 column volumes) of tris(hydroxymethyl)aminomethane buffer (50 mmolar, pH 7.8) containing sodium chloride (200 mmolar) at a flow rate of 3 liters per hour and a pressure of 0.3 atmospheres until the eluant had an absorbance less than 0.001 OD at 214 nm. The FLAG™ GG 9-mer (SEQ ID NO:20) was eluted at a flow rate of 3 liters/hour with a step gradient of buffer (50 mmolar, pH 7.8) containing sodium chloride (375 mmolar) in 500 ml fractions into 4 liters. The fractions containing the biopolymer, as determined by conventional SDS acrylamide electrophoresis, were pooled and designated fraction F1.

The FLAG™ N-terminal epitope was removed by Trypsin proteolytic cleavage at the C-terminal side of the lysine* immediately proceeding the first repeating tripeptide (GPE) in the biopolymer to produce a cleaved unwanted peptide and the desired SEQ ID NO:3. To cleave the epitope, a sample (1 g) of fraction F1 was reacted with 400 units Trypsin (type XI DPCC treated) per mg of biopolymer per ml of calcium chloride (20 mmolar) in buffer (100 mmolar, pH 8.5) at 37° C. for 18 hours. The reaction was completely dependent upon the presence of calcium chloride. The completeness of the reaction was determined to be essentially 100% by estimating the relative mobility on SDS gels of the Trypsin treated sample relative to the mobility of the starting fraction F1. The Trypsin cleaved biopolymer migrated faster on SDS acrylamide electrophoresis than the uncleaved biopolymer with a relative Rf of 1.10. The Trypsin cleaved biopolymer reaction solution was designated fraction F2. The use of Trypsin additionally provides a means to remove potential trace amounts of protein that are not detectable by standard analytical means such as absorbance at 280 nm, Coomassie Blue R-250 staining of SDS electrophoresis gels, GHOST Bands™ Protein Detection System (Promega Corporation) or silver staining of SDS electrophoresis gels.

The apparent molecular weights determined from the SDS gel migration distances relative to the molecular weight markers for the uncleaved and the cleaved biopolymers were 40 kd and 38 kd, respectively. The calculated molecular weights from the primary amino acid sequence are 27,177 daltons and 25,778 daltons, respectively. It is known for collagen and gelatin fragments that their apparent molecular weight is about 1.4 times larger than their true primary sequence molecular weight ("Estimation of the Size of Collagenous Proteins by Electrophoresis and Gel Chromatography", *Methods in Enzymology*, 1982, Vol. 82, Section 19, pp. 410–423). The ratio of the apparent molecular weight to the primary sequence molecular weight for the uncleaved and cleaved biopolymers was about 1.47 and is thus consistent with the known anomalous molecular weight behavior of collagen and gelatin fragments.

SEQ ID NO:3 stained pink with Coomassie Blue R-250 in a transitory manner only during the early phase of destaining in 10% acetic acid and 5% methanol and at the end point of destaining was not visible at all. The FLAG™ epitope on the biopolymer (SEQ ID NO:20) serves to enable detection by Coomassie Blue R-250 staining. However, the FLAG™ epitope did not enable detection by M1 or M2 monoclonal antibodies on Western blots of SDS gels. Therefore to detect the processed biopolymer without the FLAG™ epitope, SDS gels were visualized using a commercially available negative stain utilizing copper containing solutions (GHOST BANDS™ Protein Detection System).

Alternatively, to reproducibly and conveniently detect the FLAG™-containing biopolymer, the cationic carbocyanine dye, 4,5,4',5'-dibenzo-3,3'-diethyl-9-methyl-thiacarbocyanine bromide (also known as "Stains-All") was used. The noted biopolymer stained a chrome blue-green color against a pink background.

SEQ ID NO:3 from fraction F2 was purified on a FRACTOGEL™ tentacle polymer ion exchange matrix (from EM Separations, Division of EM Industries, Inc.). One gram of Trypsin cleaved biopolymer in 1 liter of fraction F2 reaction buffer mix was brought to a final ethylenediaminetetraacetic acid concentration (40 mmolar) and applied to a 5×30 cm (0.5 liter) DMAE FRACTOGEL™ tentacle polymer ion exchange column in tris(hydroxymethyl)aminomethane (50 mmolar, pH 8.0) containing sodium chloride (50 mmolar) at a cross sectional flow rate of 45 ml/hour/cm². The addition of ethylenediaminetetraacetic acid (40 mmolar) complexed the calcium chloride (20 mmolar) from the fraction F2 reaction buffer mix. The calcium chloride was observed to cause elution of the SEQ ID NO:3 biopolymer at variable sodium chloride concentrations from the FRACTOGEL™ tentacle polymer ion exchange matrix. The cleaved FLAG™ epitope peptide and Trypsin self-digestion peptide fragments were eluted with 4 column volumes of tris(hydroxymethyl)aminomethane buffer (50 mmolar, pH 8.0) containing sodium chloride (300 mmolar), as assayed by a very low ratio of $A_{214}/A_{280}$ of less than 5.

Residual uncleaved biopolymer was eluted with 2 column volumes in half column volume steps of buffer (50 mmolar, pH 8.0) containing sodium chloride (400 mmolar) as assayed by a low ratio of $A_{214}/A_{280}$ of 41. SEQ ID NO:3 was eluted in a pure form with 2 column volumes in half column volume, steps of buffer (50 mmolar, pH 8.0) containing sodium chloride (600 mmolar) as assayed by a very high ratio of $A_{214}/A_{280}$ Of 281. The fractions containing the pure biopolymer were pooled and designated fraction F3.

In order to prepare and purify the biopolymer in a form suitable for use in photographic silver halide emulsions, including the controlled formation of silver halide crystals containing tabular or other morphologies, the biopolymer was dialyzed until the residual ions were potassium cations and nitrate anions. At the concentrations involved, these ions do not change the photographic properties of silver halides, whereas the original buffer, a primary amine, may affect them. A sample (750 mg) of pure SEQ ID NO:3 biopolymer fraction F3 (at a concentration of 1 mg/ml) was brought to a final concentration of ethylenediaminetetraacetic acid (20 mmolar) and dialyzed in SPECTRAPOR Seven 3,500 molecular weight, low metal and low sulfur containing dialysis tubing three times with 20 liters of deionized water (18 Megaohms/cm), 2 times with 1 mmolar potassium nitrate and two times with deionized water (18 Megaohms/cm). The dialyzed pure biopolymer was freeze dried into a fluffy white powder and designated as fraction F4.

To prepare the dialyzed pure biopolymer in a form suitable for photographic silver halide application, it was desalted by gel chromatography to remove excess potassium and nitrate counter ions. The dialyzed fraction F4 (750 mg) was dissolved (about 0.75 w/v) into 98 ml of 0.22 µm filtered deionized water, warmed to 45° C. and held at that temperature for 30 minutes. It was then applied at a cross sectional flow rate of 45 ml/hour/cm$^2$ onto a 5 cm×18 cm (0.5 liter) G-25 Sephadex column in 0.22 µm filtered deionized water. The column was eluted in 0.22 µm filtered deionized water (18 Megaohms/cm) in a drop-wise manner into 8 ml constant drop fractions. The use of 0.22 µm filtered deionized water (18 Megaohms/cm) eliminates the possibility of particulate contaminants that might affect nucleation, growth or photographic sensitivity, of silver halide grains, including tabular grains. The G-25 desalted biopolymer eluted as expected for classical desalting chromatography at the excluded volume and with some tailing past the void volume. Strikingly, the constant drop fractions containing the G-25 desalted pure biopolymer had almost a 15% increase in volume (about 9.2 ml) compared to fractions containing water or residual desalted ions (8 ml). Constant drop fractions were pooled beginning at the excluded volume that contained pure SEQ ID NO:3 (as determined by a high ratio of $A_{214}/A_{280}$ of 281) until the fractions began to show an increase in conductivity due to the emergence of ion impurities at the void volume (as determined by conductivity). The yield was determined by the use of a molar absorption constant at 214 nm of 241,000, based on the molar absorption constant at 214 nm of the GG monomer, 26,777, scaled to the molecular weight of the GG biopolymer. Later, this molar absorption constant was determined directly on the biopolymer and found to be accurate. A total of 675 mg of desalted pure biopolymer was recovered. The liquid desalted pure biopolymer was designated fraction F5.

To deliver the liquid desalted pure biopolymer in a convenient form for photographic emulsion precipitation, fraction F5 was freeze dried. Upon freeze drying, it became a clear transparent film that did not shatter but could be torn with the release of fibrils along the torn edges. The freeze dried desalted pure biopolymer was designated fraction F6.

The freeze dried desalted pure biopolymer was characterized at the Analytical and Synthetic Facility, Cornell Biotechnology Center, for amino acid composition by standard means of acid hydrolysis, ion chromatography and fluorescent detection. The following analysis was determined:

| Amino Acid | pMolar |
| --- | --- |
| Asx | 88.3 |
| Glx | 4830 |
| Ser | 11.4 |
| Gly | 4820 |
| His | <5 |
| Arg | 6.8 |
| Thr | 14.2 |
| Ala | 16.2 |
| Pro | 4850 |
| Tyr | 18.8 |
| Val | 6.8 |
| Met | 9.7 |
| Cys | <10 |
| Ile | <5 |
| Leu | 6.5 |
| Phe | 25.2 |
| Lys | 51.7 |

SEQ ID NO:3 was found to have an amino acid composition of glycine, proline and glutamic acid in a 1:1:1 molar ratio. This composition is consistent with the predicted amino acid composition since glutamines deamidate during the acid hydrolysis sample preparation. To crudely estimate the purity of the biopolymer in this sample, one can add the amounts of all amino acids present that are not contained by the biopolymer and divide by the amount of amino acids contained by the biopolymer. The result is a purity of at least 98.6%.

The freeze dried desalted pure biopolymer was also characterized by the Analytical and Synthetic Facility, Cornell Biotechnology Center for the N-terminus amino acid sequence. It was found to have an amino acid sequence as predicted beginning after the lysine for Trypsin cleavage through the next 40 amino acids. The three glutamines in the first 40 amino acids were found to be fully amidated. It is likely that the remaining encoded glutamines in the biopolymer are amidated glutamines as well.

The FLAG™ containing biopolymer (SEQ ID NO:20) was also characterized by N-terminus amino acid sequencing. It was found to have an amino acid sequence beginning with the FLAG™ epitope and then through the first 40 amino acids of the biopolymer. This demonstrates that upon secretion of this biopolymer the Kex2p protease correctly cleaved at the C-terminal side of the encoded Lys-Arg cleavage site to correctly expose a free N-terminal FLAG™ epitope. The inability to detect the biopolymer by the M1 or M2 FLAG™ anti-antibody on Western blots as previously described is therefore for some other reason than the mere absence of the target epitope.

The freeze dried desalted pure biopolymer was also characterized at the Analytical and Synthetic Facility for molecular weight by laser desorption mass spectrometry on a commercially available FinniganMat instrument. It was found to have a molecular weight of 26,001 daltons. This agrees well (within experimental error) with the predicted 25,778 daltons. The difference in molecular weights may be because of 4 or 5 residual strongly bound calcium ions.

Preparation Method 2 for Making Biopolymer Using Chemical Synthesis:

A biopolymer of the present invention was prepared by chemical synthesis of the polypeptides (SEQ ID NO:4 and 6–14) in the following manner.

Each of the noted polypeptides was synthesized by continuous flow solid phase techniques on a commercially available Milligen Corporation Model 9050 Peptide Synthesizer using the 9-fluorenylmethoxycarbonyl (Fmoc) amino terminal protection strategy known in the art (see, for example, Atherton et al, *Solid Phase Peptide Synthesis*, IRL Press, New York, New York 1989, and Bodansky, *Principles of Peptide Synthesis*, Springer-Verlag, New York, N.Y., 1984). The solid phase peptide synthesis protocol consisted of N-1 cycles where N is the number of amino acids in the desired polypeptide. Each cycle consisted of four steps: "deblocking", "activating", "coupling" and "capping". After the final cycle, the protocol included a "cleavage/deprotection" step.

The solid phase support used in these procedures was a polyamide-kieselguhr composite having a covalently attached 4-hydroxymethylphenoxyacetic acid linking group (available as Pepsyn-KA from Milligen Corporation). This material was provided with the Fmoc protected carboxy terminal amino acid already attached. In all cases, 2.7 grams of this support material were used, slurried in a minimum volume of amine free N,N-dimethylformamide, and packed in a synthesis column (1×10 cm). A gap (0.5 cm) was left at the top of the column to allow for the expansion of the support material due to the growth of the peptide chain during synthesis. In general, the loading of the solid phase support was 0.09 milliequivalents/g of support. This was confirmed by removing the Fmoc group quantitatively from a weighted quantity of support in a known volume of 20% (v/v) piperidine in N,N-dimethylformamide. The amount of loaded amino acid was determined from the concentration of the Fmoc-piperidine adduct by measuring the absorbance of the solution at 301 nm $\epsilon_{301}=7,800$ molar$^{-1}$cm$^{-1}$.

"Deblocking Step":

The Fmoc groups were removed using a seven minute column wash of a 20% piperidine/N,N-dimethyl formamide mixture. The extent of Fmoc removal was determined by monitoring the column effluent at 313 nm by means of an on line UV detection. When all of the Fmoc had been removed, the column was washed with amine-free N,N-dimethylformamide for 12 minutes.

"Activating/Coupling Steps":

After all of the 20% piperidine was removed from the column, an acylation step (addition of the next Fmoc amino acid) was begun. The coupling strategy employed was 1-hydroxybenzotriazole mediated active ester acylation. In this approach, an excess (3.4 equivalents) of the Fmoc protected active esters was dissolved immediately before use in a small volume (2.5 ml) of 5% solution of 1-hydroxybenzotriazole in N,N-dimethylformamide.

The active ester-Hobt acylation solution was injected into the column and recirculated by means of a pump at a flow rate of about 5.0 ml/minute. The progress of the acylation was monitored by an on line UV detector at 313 nm. The standard acylation time was 30 minutes. However, this was increased when necessary to as much as 120 minutes. After coupling was complete, the acylation solution was washed from the column with an extensive N,N-dimethylformamide wash.

Two types of Fmoc protected preformed active esters of the amino acids were obtained from Milligen Corporation. For most amino acids (all except threonine and serine), pentafluorophenyl esters were employed. However, for threonine and serine, 3-hydroxy-1,2-dihydro-4-oxo-benzotriazine esters were used. The quality of the active esters was confirmed by thin layer chromatography on activated silica plates in a mixture of chloroform, methanol and acetonitrile (90:5:5 v/v ratio). The side chain protecting strategy varied with the amino acid. For example, for alanine, asparagine, glycine, isoleucine, leucine, methionine, phenylalanine, proline, tryptophan, valine and glutamine, no protection was needed. For arginine, 4-methoxy-2,3,6-trimethylbenzenesulfonyl was used for protection, and for histidine and cysteine, triphenylmethyl was used for protection. For lysine, protection was afforded by $N^{\alpha}$-t-butyloxycarbonyl and t-butyl was used for aspartic acid, glutamic acid, serine, threonine and tyrosine.

"Capping Step":

Any remaining unreacted alpha amino acid groups were then capped by washing the column for 12 minutes with a solution of acetic anhydride (0.5 molar) and pyridine (0.5 molar) in N,N-dimethylformamide. This was done to eliminate internal deletions, and to facilitate the purification of the desired product. The capping solution was removed by washing the system with N,N-dimethylformamide.

As noted above, these steps were repeated for each new amino acid added to the peptide chain. When the desired length and sequence of amino acids were reached, the synthesis was complete. The last Fmoc group was removed as described above, and the 20% piperidine solution was washed out first with N,N-dimethylformamide and then with dichloromethane.

"Cleavage/Deprotection Step":

The product polypeptide resign was removed from the column and dried under reduced pressure. The dried polypeptide was cleaved from the support, and the protective side chains removed by treatment with trifluoroacetic acid that contained a scavenger to avoid side reaction that might occur at some of the labile side chain functional groups. The polypeptide was suspended in a cleavage reagent mixture of trifluoroacetic acid, thioanisole, ethanedithiol and anisole (90:5:3:2 v/v ratio) with gentle agitation. After 2 hours, the solid support was separated from the soluble deprotected polypeptide by filtration. The solvent and scavengers were removed by roto-evaporation. The polypeptide product was precipitated with ether and chilled to 4° C., and the precipitate was spun down in a centrifuge and the ether decanted. The precipitate was then redissolved in 5% acetic acid, and extracted against 3 volumes of ether. The aqueous layer was then filtered and purified by reverse phase high pressure liquid chromatography.

The desired polypeptide product was identified by mass spectrometry and its purity was checked by two dimensions of high pressure liquid chromatography. If either of the dimensions indicated the presence of more than 5% impurities, the material was repurified. The purified material was then lyophilized and stored desiccated at −20° C.

The following examples are provided to illustrate the practice of this invention in a nonlimiting manner. Unless otherwise noted, all percentages are by weight.

EXAMPLE 1

Preparation of Photographic Emulsion Having Non-Tabular Grains

A photographic emulsion having non-tabular grains was prepared using a biopolymer as a nucleation peptizer in the following manner.

The biopolymer identified herein as SEQ ID NO:11 was prepared as described above in Preparatory Method 2. In a nucleation step, the biopolymer (at a concentration of 0.15 weight %) was added to a conventional reaction vessel along with an aqueous solution of sodium bromide (1 g/l). While the vessel was maintained at 70° C., silver nitrate (2 molar) was added over a period of three minutes along with sufficient sodium bromide (2 molar) to maintain a constant halide concentration.

Oxidized gelatin (final concentration of 0.7 weight %) was added to the reaction vessel in the growth stage, along with additional sodium bromide to provide a final concentration of 4 g/l. Additional silver nitrate was added in a conventional accelerated profile, along with sufficient sodium bromide to maintain the concentration at 4 g/l.

The resulting emulsion was examined using a scanning electron microscope, and it was determined that the silver halide grains predominantly had octahedral morphology. There was no evidence of thin tabular grains.

By comparison, the same procedure was followed to prepare a silver halide emulsion in which the biopolymer was replaced by conventional limed ossein gelatin as the peptizer. It was observed using the scanning electron microscope that the emulsion contained a mixture of octahedral and thin tabular grains.

The example demonstrates that the method of this invention can provide more uniformity in silver halide grain morphology than a conventional peptizer for certain photographic emulsions.

EXAMPLE 2

Preparation of Thin Tabular Grain Photographic Emulsion

This example is similar to Example 1 except that the biopolymer identified as SEQ ID NO:6 was used as the peptizer in grain nucleation. This biopolymer was prepared using the procedure described in Preparatory Method 2.

Following the procedure described above, it was determined that the emulsion silver halide grains were highly thin tabular grains. This demonstrates the uniformity in grain morphology provided by the present invention, and also shows that different morphologies can be obtained using specific biopolymers as the nucleation peptizers.

EXAMPLE 3

Demonstration of Grain Morphology Control

This example describes the preparation of several silver halide emulsions using several different biopolymers as peptizers, and the types of grain morphologies obtained thereby. Each biopolymer was prepared using the procedures described above in Preparatory Method 2.

The biopolymer peptizer (0.1 weight %) and an aqueous solution of sodium bromide (1.09 g/l) were added to a reaction vessel. The contents were maintained at 50° C. while silver nitrate (2 molar) was added over a period of 45 seconds, along with sufficient halide salts (2 molar, 99.5 mole % of sodium bromide and 0.5 mole % of potassium iodide) to maintain the initial halide concentration. After a 1 minute delay, additional salts were added to bring the concentration of sodium bromide to 2.69 g/l. The temperature was then raised to 60° C.

Oxidized gelatin was added to provide a concentration of 0.7 weight %. Silver nitrate (2 molar) was then added over a 40 minute period at an increasing rate, matched by sufficient salts to maintain the new halide concentration. Finally, silver nitrate was added alone, slowly, to reduce the bromide concentration by a factor of 6.

The resulting emulsions were evaluated by taking scanning electron micrographs, and the average grain morphology and dimensions were determined using conventional techniques.

The capacity (affinity) of the given biopolymer to bind silver ion was also measured at pH 6.9–7.0 as follows:

Silver nitrate ($5\times10^{-6}$ molar), potassium nitrate (0.1 molar) and the biopolymer (0.3 weight %) were mixed at 23° C. in pH 7.0 phosphate buffer solution. The "vAg" of this solution is the potential of a bare silver electrode against a Ag/AgCl reference electrode in a salt bridge assembly. For comparison purposes, the "vAg" of a similar solution without the biopolymer was measured, and the difference in vAg readings is identified as $\Delta$ vAg for the biopolymer.

Table I below lists the bipolymers used as peptizers, the resulting "major" (predominant) grain morphologies, average grain sizes, and the biopolymer binding affinities for silver ion. It is apparent that the biopolymers that bind silver ion strongly (greater than 50 $\Delta$ vAg) provide non-tabular grain morphologies, such as octahedral morphology. Weaker binding biopolymers (less than 50 $\Delta$ vAg binding affinity) provide grains with thin tabular morphology.

TABLE I

| Biopolymer Peptizer | Major Morphology | Average Size (μM) | $\Delta$ vAg |
|---|---|---|---|
| SEQ ID No: 11 | Octahedral (70%) | 0.6 | 102 |
| SEQ ID No: 12 | Irregular (60%) | 0.4 | 117 |
| SEQ ID No: 13 | Octahedral (90%) | 0.6 | 58 |
| SEQ ID No: 6 | Tabular (80%) | *1.3 × 0.055 | 28 |
| SEQ ID No: 7 | Tabular (50%) | *1.9 × 0.065 | 7 |
| SEQ ID No: 8 | Tabular (85%) | *1.3 × 0.052 | 2 |
| SEQ ID No: 9 | Tabular (85%) | *1.3 × 0.047 | 12 |
| SEQ ID No: 10 | Tabular (88%) | *1.3 × 0.047 | 2 |

*The two dimensions refer to equivalent circular diameter and grain thickness, respectively.

EXAMPLE 4

Emulsion Prepared Using a Biopolymer Prepared Using Recombinant DNA Technology The biopolymer identified herein as SEQ ID NO:3 was prepared using the recombinant DNA preparatory procedure described in the Preparatory Method 1 identified above. It was used as a nucleation peptizer to prepare an emulsion using the procedure described in Example 3 except that the biopolymer was also used as the peptizer in the growth segment of emulsion preparation in place of oxidized gelatin.

The resulting emulsion was evaluated using a scanning electron microscope, and found to have predominantly grains having a thin tabular morphology. This demonstrates the usefulness of bipolymers prepared using recombinant DNA technology to make uniform thin tabular silver halide emulsions. The emulsion grains in this emulsion had an average thickness of 0.074 μm and an average equivalent circular diameter of 0.55 μm.

The invention has been described in detail with particular reference to preferred embodiments thereof, but it will be understood that variations and modifications can be effected within the spirit and scope of the invention.

We claim:

1. A method for preparing a thin tabular silver halide emulsion in which the halide content is at least 50 mole percent silver bromide, and wherein tabular grains of less than 0.30 μm in thickness and having an aspect ratio of at least 5 account for more than 50% of the total grain projected area, said method comprising:

nucleating silver halide grains in the presence of a nucleation peptizer, and thereafter growing said silver halide grains in the presence of a growth peptizer, wherein said nucleation or growth peptizer is a synthetic polypeptide biopolymer having a specifically designed amino acid sequence and a low binding affinity for silver ion.

2. The method of claim 1 wherein said nucleation or growth peptizer is present in an amount of at least about 0.03 weight percent.

3. The method of claim 1 wherein said nucleation or growth peptizer has been prepared solely by recombinant genetic engineering using a yeast host cell.

4. The method of claim 1 wherein said nucleation or growth peptizer has been prepared solely by chemical synthesis.

5. A method for preparing a non-tabular silver halide emulsion, said method comprising:
nucleating silver halide grains in the presence of a nucleation peptizer, and thereafter growing said silver halide grains in the presence of a growth peptizer,
wherein said nucleation or growth peptizer is a synthetic polypeptide biopolymer having a specifically designed amino acid sequence and a high binding affinity for silver ion.

6. The method of claim 5 wherein said nucleation or growth peptizer is present in an amount of at least about 0.03 weight percent.

7. The method of claim 5 wherein said nucleation or growth peptizer has been prepared solely by recombinant genetic engineering using a yeast host cell.

8. The method of claim 5 wherein said nucleation or growth peptizer has been prepared solely by chemical synthesis.

9. A process for preparing a silver halide emulsion in a reaction mixture, said process comprising nucleating or growing silver halide grains in said reaction mixture in the presence of a polypeptide biopolymer nucleation or growth peptizer having at least one occurrence of a peptide sequence represented by Formulae I, II or III:

{[(Gly Pro Gln)(Gly Pro Glu)$_4$]$_2$}$_n$    I

Gly Pro Glu{[(Gly Pro Gln)(Gly Pro Glu)$_4$]$_2$}$_n$    II

Gly Pro Xaa$_1$ Gly Leu Xaa$_2$ Gly Pro Arg Gly Pro Pro Gly Ala Ser Gly Ala Pro Gly Pro Glu Gly Phe Gln Gly    III wherein
Xaa$_1$ and Xaa$_2$ are independently the amino acids identified as Met, Ile, His, Lys, Asn, Tyr or Gln, and n is 1 to 25.

10. The process of claim 9 wherein said nucleation or growth peptizer is present in said reaction mixture in an amount of at least about 0.03 weight %.

11. The process of claim 9 wherein said reaction mixture further includes a hydrophilic polymer or protein co-peptizer.

12. The process of claim 11 wherein said co-peptizer is oxidized gelatin.

13. The process of claim 9 wherein said peptide sequence is represented by Formula II wherein n is 3 to 18.

14. The process of claim 9 wherein said peptide sequence is:
SEQ ID NO:4:

{[(Gly Pro Gln)(Gly Pro Glu)$_4$]$_2$}$_1$

SEQ ID NO:1

Gly Pro Glu{[(Gly Pro Gln)(Gly Pro Glu)$_4$]$_2$}$_3$

SEQ ID NO:3:

Gly Pro Glu{[(Gly Pro Gln)(Gly Pro Glu)$_4$]$_2$}$_9$ or SEQ ID NO:5:

{[(Gly Pro Gln)(Gly Pro Glu)$_4$]$_2$}$_{18}$.

15. The process of claim 9 wherein said peptide sequence is represented by Formula III wherein each of Xaa$_1$ and Xaa$_2$ is the amino acid identified as Ile, Lys, Asn, Tyr or Gln.

16. The process of claim 9 wherein said peptide sequence is represented by Formula III wherein:
each of Xaa$_1$ and Xaa$_2$ is Met or His, or
Xaa$_1$ is Ile and Xaa$_2$ is Met, or
Xaa$_1$ is Met and Xaa$_1$ is Ile.

17. The process of claim 9 wherein said nucleation or growth peptizer has a high affinity for silver ion.

18. The process of claim 9 for preparing a thin tabular grain silver halide emulsion comprising silver halide grains in which the halide content is at least 50 mole percent silver bromide and wherein tabular grains of less than 0.30 µm in thickness and having an aspect ratio of at least 5 account for greater than 50% of the total grain projected area,
said nucleation or growth peptizer having a low binding affinity for silver ion.

19. The process of claim 18 wherein said peptide sequence is represented by Formula II wherein n is 3 to 18.

20. The process of claim 18 wherein said peptide sequence is represented by Formula III wherein each of Xaa$_1$ and Xaa$_2$ is the amino acid identified as Ile, Lys, Asn, Tyr or Gln.

21. The process of claim 20 wherein said peptide sequence is represented by Formula III wherein each of Xaa$_1$ and Xaa$_2$ is Gln.

22. The process of claim 18 wherein said tabular grains account for greater than 90% of the total grain projected area.

23. The process of claim 18 wherein said tabular grains have an average thickness of less than about 0.20 µm, and the aspect ratio is from about 6 to about 100.

24. A silver halide emulsion prepared by the process of claim 9.

25. A thin tabular grain silver halide emulsion prepared by the process of claim 1.

26. A photographic element comprising a support having thereon at least one imagewise exposable layer, said layer comprising a thin tabular silver halide emulsion prepared by the process of claim 1.

27. A photographic element comprising a support having thereon at least one imagewise exposable layer, said layer comprising a non-tabular silver halide emulsion prepared by the process of claim 5.

28. A photographic element comprising a support having thereon at least one imagewise exposable layer, said layer comprising a silver halide emulsion prepared by the process of claim 9.

* * * * *